United States Patent
Kaifosh et al.

(10) Patent No.: US 10,496,168 B2
(45) Date of Patent: Dec. 3, 2019

(54) CALIBRATION TECHNIQUES FOR HANDSTATE REPRESENTATION MODELING USING NEUROMUSCULAR SIGNALS

(71) Applicant: CTRL-labs Corporation, New York, NY (US)

(72) Inventors: Patrick Kaifosh, New York, NY (US); Tudor Giurgica-Tiron, Stanford, CA (US); Adam Berenzweig, Brooklyn, NY (US); Steven Kober, New York, NY (US); Adam Al-natsheh, New York, NY (US); Alexandre Barachant, Brooklyn, NY (US); Zhuo Wang, Forest Hills, NY (US)

(73) Assignee: CTRL-labs Corporation, New York, NY (US)

( * ) Notice: Subject to any disclaimer, the term of this patent is extended or adjusted under 35 U.S.C. 154(b) by 0 days.

(21) Appl. No.: 16/257,979

(22) Filed: Jan. 25, 2019

(65) Prior Publication Data
US 2019/0227627 A1 Jul. 25, 2019

Related U.S. Application Data

(60) Provisional application No. 62/621,838, filed on Jan. 25, 2018.

(51) Int. Cl.
*G06F 3/01* (2006.01)
*A61B 5/00* (2006.01)
(Continued)

(52) U.S. Cl.
CPC ............ *G06F 3/015* (2013.01); *A61B 5/6824* (2013.01); *G06F 3/017* (2013.01);
(Continued)

(58) Field of Classification Search
None
See application file for complete search history.

(56) References Cited

U.S. PATENT DOCUMENTS

| 4,896,120 A | 1/1990 | Kamil |
| 5,625,577 A | 4/1997 | Kunii et al. |

(Continued)

FOREIGN PATENT DOCUMENTS

| CA | 2902045 A1 | 8/2014 |
| CA | 2921954 A1 | 2/2015 |

(Continued)

OTHER PUBLICATIONS

International Search Report and Written Opinion for International Application No. PCT/US2017/043686 dated Oct. 6, 2017.

(Continued)

*Primary Examiner* — Yingchun He
(74) *Attorney, Agent, or Firm* — Wolf, Greenfield & Sacks, P.C.

(57) ABSTRACT

Methods and apparatus for calibrating performance of one or more statistical models used to generate a musculoskeletal representation. The method comprises controlling presentation of instructions via a user interface to instruct the user to perform the at least one gesture and updating at least one parameter of the one or more statistical models based, at least in part on a plurality of neuromuscular signals recorded by a plurality of neuromuscular sensors during performance of the at least one gesture by the user.

28 Claims, 7 Drawing Sheets

(51) Int. Cl.
*A61B 5/11* (2006.01)
*A61B 5/04* (2006.01)
*A61B 5/0492* (2006.01)

(52) U.S. Cl.
CPC ....... *A61B 5/04004* (2013.01); *A61B 5/04012* (2013.01); *A61B 5/0492* (2013.01); *A61B 5/1107* (2013.01); *A61B 5/1112* (2013.01); *A61B 5/1114* (2013.01)

(56) References Cited

U.S. PATENT DOCUMENTS

| | | | |
|---|---|---|---|
| 6,005,548 A | 12/1999 | Latypov et al. | |
| 6,009,210 A | 12/1999 | Kand | |
| 6,244,873 B1 | 6/2001 | Hill et al. | |
| 6,411,843 B1 | 6/2002 | Zarychta | |
| 6,658,287 B1 | 12/2003 | Litt et al. | |
| 6,720,984 B1 | 4/2004 | Jorgensen et al. | |
| 6,774,885 B1 | 8/2004 | Even-Zohar | |
| 6,942,621 B2 | 9/2005 | Avinash et al. | |
| 7,089,148 B1 | 8/2006 | Bachmann et al. | |
| 7,351,975 B2 | 4/2008 | Brady et al. | |
| 7,574,253 B2 | 8/2009 | Edney et al. | |
| 7,580,742 B2 | 8/2009 | Tan et al. | |
| 7,787,946 B2 | 8/2010 | Stahmann et al. | |
| 7,805,386 B2 | 9/2010 | Greer | |
| 7,901,368 B2 | 3/2011 | Flaherty et al. | |
| 8,170,656 B2 | 5/2012 | Tan et al. | |
| 8,190,249 B1 | 5/2012 | Gharieb et al. | |
| 8,311,623 B2 | 11/2012 | Sanger | |
| 8,351,651 B2 | 1/2013 | Lee | |
| 8,421,634 B2 | 4/2013 | Tan et al. | |
| 8,435,191 B2 | 5/2013 | Barboutis et al. | |
| 8,437,844 B2 | 5/2013 | Syed Momen et al. | |
| 8,447,704 B2 | 5/2013 | Tan et al. | |
| 8,484,022 B1 | 7/2013 | Vanhoucke | |
| 8,718,980 B2 | 5/2014 | Garudadri et al. | |
| 8,744,543 B2 | 6/2014 | Li et al. | |
| 8,754,862 B2 | 6/2014 | Zaliva | |
| 8,880,163 B2 | 11/2014 | Barachant et al. | |
| 8,890,875 B2 | 11/2014 | Jammes et al. | |
| 8,892,479 B2 | 11/2014 | Tan et al. | |
| 9,037,530 B2 | 5/2015 | Tan et al. | |
| 9,218,574 B2 | 12/2015 | Phillipps et al. | |
| 9,235,934 B2 | 1/2016 | Mandella et al. | |
| 9,240,069 B1 | 1/2016 | Li | |
| 9,278,453 B2 | 3/2016 | Assad | |
| 9,299,248 B2 | 3/2016 | Lake et al. | |
| 9,367,139 B2 | 6/2016 | Ataee et al. | |
| 9,372,535 B2 | 6/2016 | Bailey et al. | |
| 9,389,694 B2 | 7/2016 | Ataee et al. | |
| 9,408,316 B2 | 8/2016 | Bailey et al. | |
| 9,459,697 B2 | 10/2016 | Bedikian et al. | |
| 9,483,123 B2 | 11/2016 | Aleem et al. | |
| 9,597,015 B2 | 3/2017 | McNames et al. | |
| 9,600,030 B2 | 3/2017 | Bailey et al. | |
| 9,612,661 B2 | 4/2017 | Wagner et al. | |
| 9,613,262 B2 | 4/2017 | Holz | |
| 9,659,403 B1 | 5/2017 | Horowitz | |
| 9,687,168 B2 | 6/2017 | John | |
| 9,696,795 B2 | 7/2017 | Marcolina et al. | |
| 9,720,515 B2 | 8/2017 | Wagner et al. | |
| 9,741,169 B1 | 8/2017 | Holz | |
| 9,766,709 B2 | 9/2017 | Holz | |
| 9,785,247 B1 | 10/2017 | Horowitz et al. | |
| 9,788,789 B2 | 10/2017 | Bailey | |
| 9,864,431 B2 | 1/2018 | Keskin et al. | |
| 9,867,548 B2 | 1/2018 | Le et al. | |
| 9,880,632 B2 | 1/2018 | Ataee et al. | |
| 9,891,718 B2 | 2/2018 | Connor | |
| 10,042,422 B2 | 8/2018 | Morun et al. | |
| 10,070,799 B2 | 9/2018 | Ang et al. | |
| 10,101,809 B2 | 10/2018 | Morun et al. | |
| 10,152,082 B2 | 12/2018 | Bailey | |
| 10,188,309 B2 | 1/2019 | Morun et al. | |
| 10,199,008 B2 | 2/2019 | Aleem et al. | |
| 10,203,751 B2 | 2/2019 | Keskin et al. | |
| 10,216,274 B2 | 2/2019 | Chapeskie et al. | |
| 2003/0144829 A1 | 7/2003 | Geatz et al. | |
| 2003/0171921 A1 | 9/2003 | Manabe et al. | |
| 2004/0092839 A1 | 5/2004 | Shin et al. | |
| 2007/0172797 A1 | 7/2007 | Hada et al. | |
| 2007/0256494 A1 | 11/2007 | Nakamura et al. | |
| 2007/0285399 A1 | 12/2007 | Lund | |
| 2008/0052643 A1 | 2/2008 | Ike et al. | |
| 2008/0214360 A1 | 9/2008 | Stirling et al. | |
| 2008/0221487 A1 | 9/2008 | Zohar et al. | |
| 2009/0082692 A1 | 3/2009 | Hale et al. | |
| 2009/0082701 A1 | 3/2009 | Zohar et al. | |
| 2009/0112080 A1 | 4/2009 | Matthews | |
| 2009/0326406 A1* | 12/2009 | Tan | G06F 3/015 600/546 |
| 2009/0327171 A1 | 12/2009 | Tan et al. | |
| 2010/0030532 A1 | 2/2010 | Arora et al. | |
| 2010/0063794 A1 | 3/2010 | Hernandez-Rebollar | |
| 2010/0106044 A1 | 4/2010 | Linderman | |
| 2010/0280628 A1 | 11/2010 | Sankai | |
| 2010/0292617 A1 | 11/2010 | Lei et al. | |
| 2010/0293115 A1 | 11/2010 | Seyed Momen | |
| 2010/0315266 A1 | 12/2010 | Gunawardana et al. | |
| 2011/0077484 A1 | 3/2011 | Van Slyke et al. | |
| 2011/0092826 A1 | 4/2011 | Lee et al. | |
| 2012/0066163 A1 | 3/2012 | Balls et al. | |
| 2012/0188158 A1 | 7/2012 | Tan et al. | |
| 2012/0265480 A1 | 10/2012 | Oshima | |
| 2012/0283526 A1 | 11/2012 | Gommesen et al. | |
| 2013/0077820 A1 | 3/2013 | Marais et al. | |
| 2013/0141375 A1 | 6/2013 | Ludwig et al. | |
| 2013/0207889 A1 | 8/2013 | Chang et al. | |
| 2013/0217998 A1 | 8/2013 | Mahfouz et al. | |
| 2013/0232095 A1 | 9/2013 | Tan et al. | |
| 2013/0317382 A1 | 11/2013 | Le | |
| 2013/0317648 A1 | 11/2013 | Assad | |
| 2014/0052150 A1 | 2/2014 | Taylor et al. | |
| 2014/0092009 A1 | 4/2014 | Yen et al. | |
| 2014/0098018 A1 | 4/2014 | Kim et al. | |
| 2014/0196131 A1 | 7/2014 | Lee | |
| 2014/0198034 A1 | 7/2014 | Bailey et al. | |
| 2014/0198035 A1 | 7/2014 | Bailey et al. | |
| 2014/0223462 A1 | 8/2014 | Aimone et al. | |
| 2014/0240103 A1 | 8/2014 | Lake et al. | |
| 2014/0240223 A1 | 8/2014 | Lake et al. | |
| 2014/0245200 A1 | 8/2014 | Holz | |
| 2014/0249397 A1 | 9/2014 | Lake et al. | |
| 2014/0278441 A1 | 9/2014 | Ton et al. | |
| 2014/0304665 A1 | 10/2014 | Holz | |
| 2014/0334083 A1 | 11/2014 | Bailey | |
| 2014/0344731 A1 | 11/2014 | Holz | |
| 2014/0355825 A1 | 12/2014 | Kim et al. | |
| 2014/0365163 A1 | 12/2014 | Jallon | |
| 2014/0376773 A1 | 12/2014 | Holz | |
| 2015/0006120 A1 | 1/2015 | Sett et al. | |
| 2015/0010203 A1 | 1/2015 | Muninder et al. | |
| 2015/0025355 A1 | 1/2015 | Bailey et al. | |
| 2015/0029092 A1 | 1/2015 | Holz et al. | |
| 2015/0035827 A1 | 2/2015 | Yamaoka et al. | |
| 2015/0045699 A1 | 2/2015 | Mokaya et al. | |
| 2015/0051470 A1 | 2/2015 | Bailey et al. | |
| 2015/0057770 A1 | 2/2015 | Bailey et al. | |
| 2015/0070270 A1 | 3/2015 | Bailey et al. | |
| 2015/0070274 A1 | 3/2015 | Morozov | |
| 2015/0084860 A1 | 3/2015 | Aleem et al. | |
| 2015/0109202 A1 | 4/2015 | Ataee et al. | |
| 2015/0124566 A1 | 5/2015 | Lake et al. | |
| 2015/0128094 A1 | 5/2015 | Baldwin et al. | |
| 2015/0141784 A1 | 5/2015 | Morun et al. | |
| 2015/0148641 A1 | 5/2015 | Morun et al. | |
| 2015/0157944 A1 | 6/2015 | Gottlieb | |
| 2015/0169074 A1 | 6/2015 | Ataee et al. | |
| 2015/0193949 A1 | 7/2015 | Katz et al. | |
| 2015/0234426 A1 | 8/2015 | Bailey et al. | |
| 2015/0261306 A1 | 9/2015 | Lake | |
| 2015/0261318 A1 | 9/2015 | Scavezze et al. | |
| 2015/0277575 A1 | 10/2015 | Ataee et al. | |

(56) References Cited

U.S. PATENT DOCUMENTS

| | | |
|---|---|---|
| 2015/0302168 A1 | 10/2015 | De Sapio et al. |
| 2015/0309563 A1* | 10/2015 | Connor .................. G06F 3/011 73/865.4 |
| 2015/0309582 A1 | 10/2015 | Gupta |
| 2015/0313496 A1* | 11/2015 | Connor ............... A61B 5/0476 600/301 |
| 2015/0325202 A1 | 11/2015 | Lake et al. |
| 2015/0346701 A1 | 12/2015 | Gordon et al. |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0187992 A1 | 6/2016 | Yamamoto et al. |
| 2016/0235323 A1 | 8/2016 | Tadi et al. |
| 2016/0262687 A1 | 9/2016 | Imperial et al. |
| 2016/0274758 A1 | 9/2016 | Bailey |
| 2016/0292497 A1 | 10/2016 | Kehtarnavaz et al. |
| 2016/0313798 A1 | 10/2016 | Connor |
| 2016/0313801 A1 | 10/2016 | Wagner et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0061817 A1 | 3/2017 | Mettler May |
| 2017/0080346 A1 | 3/2017 | Abbas |
| 2017/0090604 A1 | 3/2017 | Barbier |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0188980 A1 | 7/2017 | Ash |
| 2017/0259167 A1 | 9/2017 | Cook et al. |
| 2017/0308118 A1 | 10/2017 | Ito |
| 2018/0020951 A1 | 1/2018 | Kaifosh et al. |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0088765 A1 | 3/2018 | Bailey |
| 2018/0095630 A1 | 4/2018 | Bailey |
| 2018/0101289 A1 | 4/2018 | Bailey |
| 2018/0120948 A1 | 5/2018 | Aleem et al. |
| 2018/0150033 A1 | 5/2018 | Lake et al. |
| 2018/0153430 A1* | 6/2018 | Ang .................... A61B 5/0488 |
| 2018/0153444 A1 | 6/2018 | Yang et al. |
| 2018/0154140 A1 | 6/2018 | Bouton et al. |
| 2018/0307314 A1 | 10/2018 | Connor |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0025919 A1 | 1/2019 | Tadi et al. |
| 2019/0038166 A1 | 2/2019 | Tavabi et al. |
| 2019/0076716 A1 | 3/2019 | Chiou et al. |
| 2019/0121305 A1 | 4/2019 | Kaifosh et al. |
| 2019/0121306 A1 | 4/2019 | Kaifosh et al. |
| 2019/0150777 A1 | 5/2019 | Guo et al. |

FOREIGN PATENT DOCUMENTS

| | | |
|---|---|---|
| CA | 2939644 A1 | 8/2015 |
| CN | 1838933 A | 9/2006 |
| CN | 105190578 A | 12/2015 |
| CN | 106102504 A | 11/2016 |
| EP | 2 198 521 B1 | 6/2012 |
| EP | 2 959 394 A1 | 12/2015 |
| EP | 3 104 737 A1 | 12/2016 |
| JP | H05-277080 A | 10/1993 |
| JP | 2005-095561 A | 4/2005 |
| JP | 2010-520561 A | 6/2010 |
| JP | 2016-507851 A | 3/2016 |
| JP | 2017-509386 A | 4/2017 |
| KR | 2015-0123254 A | 11/2015 |
| KR | 2016-0121552 A | 10/2016 |
| KR | 10-1790147 B1 | 10/2017 |
| WO | WO 2008/109248 A2 | 9/2008 |
| WO | WO 2009/042313 A1 | 4/2009 |
| WO | WO 2014/130871 A1 | 8/2014 |
| WO | WO 2014/186370 A1 | 11/2014 |
| WO | WO 2014/194257 A1 | 12/2014 |
| WO | WO 2014/197443 A1 | 12/2014 |
| WO | WO 2015/027089 A1 | 2/2015 |
| WO | WO 2015/073713 A1 | 5/2015 |
| WO | WO 2015/081113 A1 | 6/2015 |
| WO | WO 2015/123445 A1 | 8/2015 |
| WO | WO 2015/199747 A1 | 12/2015 |
| WO | WO 2016/041088 A1 | 3/2016 |
| WO | WO 2017/062544 A1 | 4/2017 |
| WO | WO 2017/092225 A1 | 6/2017 |
| WO | WO 2017/120669 A1 | 7/2017 |
| WO | WO 2017/172185 A1 | 10/2017 |

OTHER PUBLICATIONS

International Preliminary Report on Patentability for International Application No. PCT/US2017/043686 dated Feb. 7, 2019.
International Search Report and Written Opinion for International Application No. PCT/US2017/043693 dated Oct. 6, 2017.
International Preliminary Report on Patentability for International Application No. PCT/US2017/043693 dated Feb. 7, 2019.
International Search Report and Written Opinion for International Application No. PCT/US2017/043791 dated Oct. 5, 2017.
International Preliminary Report on Patentability for International Application No. PCT/US2017/043791 dated Feb. 7, 2019.
International Search Report and Written Opinion for International Application No. PCT/US2017/043792 dated Oct. 5, 2017.
International Preliminary Report on Patentability for International Application No. PCT/US2017/043792 dated Feb. 7, 2019.
International Search Report and Written Opinion for International Application No. PCT/US2018/056768 dated Jan. 15, 2019.
International Search Report and Written Opinion for International Application No. PCT/US2018/061409 dated Mar. 12, 2019.
International Search Report and Written Opinion for International Application No. PCT/US2018/063215 dated Mar. 21, 2019.
Benko et al., Enhancing Input on and Above the Interactive Surface with Muscle Sensing. The ACM International Conference on Interactive Tabletops and Surfaces. ITS '09. 2009:93-100.
Boyali et al., Spectral Collaborative Representation based Classification for hand gestures recognition on electromyography signals. Biomedical Signal Processing and Control. 2016;24:11-18.
Cheng et al., A Novel Phonology- and Radical-Coded Chinese Sign Language Recognition Framework Using Accelerometer and Surface Electromyography Sensors. Sensors. 2015;15:23303-24.
Csapo et al., Evaluation of Human-Myo Gesture Control Capabilities in Continuous Search and Select Operations. 7th IEEE International Conference on Cognitive Infocommunications. 2016;000415-20.
Delis et al., Development of a Myoelectric Controller Based on Knee Angle Estimation. Biodevices 2009. International Conference on Biomedical Electronics and Devices. Jan. 17, 2009. 7 pages.
Diener et al., Direct conversion from facial myoelectric signals to speech using Deep Neural Networks. 2015 International Joint Conference on Neural Networks (IJCNN). Oct. 1, 2015. 7 pages.
Ding et al., HMM with improved feature extraction-based feature parameters for identity recognition of gesture command operators by using a sensed Kinect-data stream. Neurocomputing. 2017;262:108-19.
Farina et al., Man/machine interface based on the discharge timings of spinal motor neurons after targeted muscle reinnervation. Nature. Biomedical Engineering. 2017;1:1-12.
Gallina et al., Surface EMG Biofeedback. Surface Electromyography: Physiology, Engineering, and Applications. 2016:485-500.
Jiang, Purdue University Graduate School Thesis/Dissertation Acceptance. Graduate School Form 30. Updated Jan. 15, 2015. 24 pages.
Kawaguchi et al., Estimation of Finger Joint Angles Based on Electromechanical Sensing of Wrist Shape. IEEE Transactions on Neural Systems and Rehabilitation Engineering. 2017;25(9):1409-18.

(56) References Cited

OTHER PUBLICATIONS

Kim et al., Real-Time Human Pose Estimation and Gesture Recognition from Depth Images Using Superpixels and SVM Classifier. Sensors. 2015;15:12410-27.

Koerner, Design and Characterization of the Exo-Skin Haptic Device: A Novel Tendon Actuated Textile Hand Exoskeleton. 2017. 5 pages.

Li et al., Motor Function Evaluation of Hemiplegic Upper-Extremities Using Data Fusion from Wearable Inertial and Surface EMG Sensors. Sensors. MDPI. 2017;17(582):1-17.

Mcintee, A Task Model of Free-Space Movement-Based Geastures. Dissertation. Graduate Faculty of North Carolina State University. Computer Science. 2016. 129 pages.

Naik et al., Source Separation and Identification issues in bio signals: A solution using Blind source seperation. Intech. 2009. 23 pages.

Naik et al., Subtle Hand gesture identification for HCI using Temporal Decorrelation Source Separation BSS of surface EMG. Digital Image Computing Techniques and Applications. IEEE Computer Society. 2007;30-7.

Negro et al., Multi-channel intramuscular and surface EMG decomposition by convolutive blind source separation. Journal of Neural Engineering. 2016;13:1-17.

Saponas et al., Demonstrating the Feasibility of Using Forearm Electromyography for Muscle-Computer Interfaces. CHI 2008 Proceedings. Physiological Sensing for Input. 2008:515-24.

Saponas et al., Enabling Always-Available Input with Muscle-Computer Interfaces. UIST '09. 2009:167-76.

Saponas et al., Making Muscle-Computer Interfaces More Practical. CHI 2010: Brauns and Brawn. 2010:851-4.

Sauras-Perez et al., A Voice and Pointing Gesture Interaction System for Supporting Human Spontaneous Decisions in Autonomous Cars. Clemson University. All Dissertations. 2017. 174 pages.

Shen et al., I am a Smartwatch and I can Track my User's Arm. University of Illinois at Urbana-Champaign. MobiSys' 16.

Son et al., Evaluating the utility of two gestural discomfort evaluation methods. PLOS One. 2017. 21 pages.

Strbac et al., Microsoft Kinect-Based Artificial Perception System for Control of Functional Electrical Stimulation Assisted Grasping. Hindawi Publishing Corporation. BioMed Research International. 2014. 13 pages.

Torres, Myo Gesture Control Armband. PCMag. Https://www.pcmag.com/article2/0,2817,2485462,00.asp 2015. 9 pages.

Wodzinski et al., Sequential Classification of Palm Gestures Based on A* Algorithm and MLP Neural Network for Quadrocopter Control. Metrol. Meas. Syst., 2017;24(2):265-76.

Xue et al., Multiple Sensors Based Hand Motion Recognition Using Adaptive Directed Acyclic Graph. Applied Sciences. MDPI. 2017;7(358):1-14.

International Search Report and Written Opinion for International Application No. PCT/US2019/015134 dated May 15, 2019.

International Search Report and Written Opinion for International Application No. PCT/US2019/015167 dated May 21, 2019.

International Search Report and Written Opinion for International Application No. PCT/US2019/015174 dated May 21, 2019.

International Search Report and Written Opinion for International Application No. PCT/US2019/015238 dated May 16, 2019.

International Search Report and Written Opinion for International Application No. PCT/US2019/015183 dated May 3, 2019.

International Search Report and Written Opinion for International Application No. PCT/US2019/015180 dated May 28, 2019.

International Search Report and Written Opinion for International Application No. PCT/US2019/015244 dated May 16, 2019.

International Search Report and Written Opinion for International Application No. PCT/US19/20065 dated May 16, 2019.

Arkenbout et al., Robust Hand Motion Tracking Through Data Fusion of 5Dt Data Glove and Nimble VR Kinect Camera Measurements. Sensors. 2015;15:31644-71.

Davoodi et al., Development of a Physics-Based Target Shooting Game to Train Amputee Users of Multijoint Upper Limb Prostheses. Presence. Massachusetts Institute of Technology. 2012;21(1):85-95.

Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.

Hauschild et al., A Virtual Reality Environment for Designing and Fitting Neural Prosthetic Limbs. IEEE Transactions on Neural Systems and Rehabilitation Engineering. 2007;15(1):9-15.

Lee et al., Motion and Force Estimation System of Human Fingers. Journal of Institute of Control, Robotics and Systems. 2011;17(10):1014-1020.

Lopes et al., Hand/arm gesture segmentation by motion using IMU and EMG sensing. ScienceDirect. Elsevier. Procedia Manufacturing. 2017;11:107-13.

Martin et al., A Novel Approach of Prosthetic Arm Control using Computer Vision, Biosignals, and Motion Capture. IEEE. 2014. 5 pages.

Mendes et al., Sensor Fusion and Smart Sensor in Sports and Biomedical Applications. Sensors. 2016;16(1569):1-31.

Sartori et al., Neural Data-Driven Musculoskeletal Modeling for Personalized Neurorehabilitation Technologies. IEEE Transactions on Biomedical Engineering. 2016;63(5):879-93.

PCT/US2019/015134, dated May 15, 2019, International Search Report and Written Opinion.

PCT/US2019/015167, dated May 21, 2019, International Search Report and Written Opinion.

PCT/US2019/015174, dated May 21, 2019, International Search Report and Written Opinion.

PCT/US2019/015238, dated May 16, 2019, International Search Report and Written Opinion.

PCT/US2019/015183, dated May 3, 2019, International Search Report and Written Opinion.

PCT/US2019/015180, dated May 28, 2019, International Search Report and Written Opinion.

PCT/US2019/015244, dated May 16, 2019, International Search Report and Written Opinion.

PCT/US19/20065, dated May 16, 2019, International Search Report and Written Opinion.

* cited by examiner

CALIBRATION TECHNIQUES FOR HANDSTATE REPRESENTATION MODELING USING NEUROMUSCULAR SIGNALS

RELATED APPLICATIONS

This application claims priority under 35 U.S.C. § 119(e) to U.S. Provisional Application Ser. No. 62/621,838, entitled "CALIBRATION TECHNIQUES FOR HANDSTATE REPRESENTATION MODELING USING NEUROMUSCULAR SIGNALS," filed on Jan. 25, 2018, which is incorporated by reference in its entirety.

BACKGROUND

In some computer applications that generate musculoskeletal representations of the human body, it is desirable for the application to know or infer the spatial positioning, orientation and movement of a user's body to provide a realistic representation of body movement. For example, in a virtual reality (VR) environment, tracking the spatial position of the user's hand enables the application to represent hand motion in the VR environment, which allows the user to interact with (e.g., by grasping or manipulating) virtual objects within the VR environment. Some existing techniques for tracking movements of a user's body using wearable sensors include using information obtained from multiple Inertial Measurement Units (IMUs) affixed to different parts of the user's body, and using external imaging devices (e.g., fixed-position cameras) to reconstruct the position and orientation of parts of the user's body.

SUMMARY

Some embodiments are directed to predicting information about the positioning and movements of portions of a user's body (e.g., arm and/or hand) represented as a multi-segment articulated rigid body system with joints connecting the multiple segments of the rigid body system. Signals recorded by wearable neuromuscular sensors placed at locations on the user's body are provided as input to a statistical model trained to predict estimates of the position (e.g., absolute position, relative position, orientation) and forces associated with a plurality of rigid segments in a computer-based representation (e.g., a musculoskeletal representation associated with a hand) when a user performs one or more movements. The combination of position information and force information associated with segments of a musculoskeletal representation associated with a hand is colloquially referred to herein as a "handstate" of the musculoskeletal representation. As a user performs different movements, a trained statistical model interprets neuromuscular signals recorded by the wearable neuromuscular sensors into position and force estimates (handstate information) that are used to update the computer-based representation. As the neuromuscular signals are continuously recorded, the computer-based representation is updated in real time and a visual representation (e.g., of a hand within a virtual reality environment) is optionally rendered based on the current handstate estimates.

Other embodiments are directed to a computerized system configured to calibrate performance of one or more statistical models used to generate a musculoskeletal representation. The system comprises a user interface configured to instruct a user to perform at least one gesture while wearing a wearable device having a plurality of neuromuscular sensors arranged thereon, and at least one computer processor. The at least one computer processor is programmed to control presentation of instructions via the user interface to instruct the user to perform the at least one gesture; and update at least one parameter of the one or more statistical models based, at least in part on a plurality of neuromuscular signals recorded by the plurality of neuromuscular sensors during performance of the at least one gesture by the user.

Other embodiments are directed to a computerized system configured to calibrate performance of one or more statistical models used to generate a musculoskeletal representation. The system comprises at least one computer processor programmed to identify, based on an output of the one or more statistical models, at least one gesture characteristic that the one or more statistical model is poor at estimating, initiate a calibration routine to update at least one parameter of the one or more statistical models to improve the performance of the one or more statistical models to accurately predict the at least one identified gesture characteristic, receive a plurality of neuromuscular signals recorded by a plurality of neuromuscular sensors during performance of at least one gesture that includes the at least one gesture characteristic, and update the at least one parameter of the one or more statistical models based, at least in part on a plurality of neuromuscular signals recorded by the neuromuscular sensors during performance of the at least one gesture by the user.

In one aspect, the at least one computer processor is further programmed to update at least one parameter of the one or more statistical models based, at least in part, on predetermined estimates of one or more of position information, force information, and neuromuscular information for the at least one gesture.

In another aspect, the at least one computer processor is further programmed to: control at least one external device to capture at least one measurement of position and/or force information during performance of the at least one gesture; and update the at least one parameter of the one or more statistical models based, at least in part, on the at least one measurement of position and/or force information.

In another aspect, the at least one external device comprises an imaging device configured to capture at least one image, and the at least one measurement of position is determined based, at least in part, on the at least one image.

In another aspect, the at least one external device comprises an inertial measurement unit.

In another aspect, the at least one external device comprises a plurality of external devices, each of which is configured to capture at least one measurement of position and/or force information during performance of the at least one gesture, and the at least one computer processor is further programmed to: combine the at least one measurement of position and/or force information captured by each of the plurality of external devices; and update the at least one parameter of the one or more statistical models based, at least in part, on the combined measurements of position and/or force.

In another aspect, updating the at least one parameter of the one or more statistical models comprises training the one or more statistical models based, at least in part, on the plurality of neuromuscular signals recorded by the neuromuscular sensors during performance of the at least one gesture by the user.

In another aspect, the one or more statistical models include a trained statistical model, and updating the at least one parameter of the one or more statistical models comprises adjusting one or more parameters provided as input to the trained statistical model without retraining the trained statistical model.

In another aspect, the at least one computer processor is further programmed to provide feedback to the user, and the feedback indicates to the user whether the performance of the at least one gesture has been performed as instructed.

In another aspect, providing feedback to the user comprises providing visual feedback.

In another aspect, instructing the user to perform at least one gesture comprises instructing the user to perform a predetermined set of gestures.

In another aspect, controlling presentation of the instructions via the user interface comprises instructing the user to perform the gestures of the predetermined set in succession.

In another aspect, the at least one computer processor is further programmed to select a new gesture to be performed by the user.

In another aspect, selecting a new gesture to be performed by the user comprises randomly selecting the new gesture from a set of gestures.

In another aspect, selecting a new gesture to be performed by the user comprises selecting a gesture previously performed by the user.

In another aspect, the at least one computer processor is further programmed to: identify, based on an output of the one or more statistical models, at least one gesture characteristic that the one or more statistical model is poor at estimating; and select the new gesture to be performed by the user based on the identified at least one gesture characteristic.

In another aspect, the at least one gesture characteristic comprises a plurality of gesture characteristics, and selecting the new gesture to be performed by the user based on the identified at least one gesture characteristic comprises selecting a new gesture that includes the plurality of gesture characteristics.

In another aspect, each of a first gesture and a second gesture in a set of gestures includes at least two of the plurality of gesture characteristics, and selecting the new gesture to be performed by the user comprises selecting the first gesture as the new gesture when the first gesture includes more of the plurality of gesture characteristics than the second gesture.

In another aspect, the at least one computer processor is further programmed to: control presentation of instructions via the user interface to instruct the user to perform the new gesture; and update at least one parameter of the one or more statistical models based, at least in part on the plurality of neuromuscular signals recorded by the neuromuscular sensors during performance of the new gesture by the user.

In another aspect, the instructions provided via the user interface includes at least one user-interpretable instruction.

In another aspect, the at least one user-interpretable instruction comprises a percentage of force exerted by one or more portions of a hand of the user.

In another aspect, the at least one user-interpretable instruction comprises a percentage of maximum force exerted by pinching at least two fingers of the hand.

In another aspect, the at least one computer processor is further programmed to provide feedback to the user, wherein the feedback indicates to the user a response of the one or more statistical models to performance of the at least one gesture by the user based on the user-interpretable instruction.

In another aspect, the at least one computer processor is further programmed to render a visual representation associated with the hand based on an output of the one or more statistical models.

In another aspect, the output of the one or more statistical models comprises position and force estimates, and rendering the visual representation associated with the hand comprises rendering at least one force metric based on the force estimates on the visual representation associated with the hand.

In another aspect, the at least one computer processor is further programmed to provide feedback to the user describing information about the accuracy and/or completeness of the at least one gesture.

In another aspect, the visual representation is rendered during the updating of the at least one parameter of the one or more statistical models.

In another aspect, the at least one computer processor is further programmed to: continuously track a calibration of a performance of the one or more statistical models during usage of the one or more statistical models following training; and initiate a calibration routine when the calibration of the performance deviates from an acceptable calibration threshold by a particular amount.

In another aspect, initiating a calibration routine comprises: controlling presentation of instructions via the user interface to instruct the user to perform one or more additional gestures that includes at least one gesture characteristic for which performance of the one or more statistical models is poor, and updating at least one parameter of at least one of the one or more statistical models based, at least in part, on the plurality of neuromuscular signals recorded by the neuromuscular sensors during performance of the one or more additional gestures by the user.

In another aspect, the musculoskeletal representation is a musculoskeletal representation associated with a hand, and the one or more statistical model are configured to output position and force estimates used to update the musculoskeletal representation associated with the hand.

In another aspect, updating at least one parameter of the one or more statistical models comprises updating a plurality of model parameters, and the at least one computer processor is further programmed to: store a user profile that includes user-specific calibration parameters, wherein the user-specific calibration parameters includes a subset of the plurality of model parameters.

In another aspect, the user-specific calibration parameters include at least one joint stiffness parameter.

Other embodiments are directed to a computerized system configured to calibrate performance of one or more statistical models used to generate a musculoskeletal representation, the system comprising: at least one computer processor programmed to: identify, based on an output of the one or more statistical models, at least one gesture characteristic that the one or more statistical model is poor at estimating; initiate a calibration routine to update at least one parameter of the one or more statistical models to improve the performance of the one or more statistical models to accurately predict the at least one identified gesture characteristic; receive a plurality of neuromuscular signals recorded by a plurality of neuromuscular sensors during performance of at least one gesture that includes the at least one gesture characteristic; and update the at least one parameter of the one or more statistical models based, at least in part, on a plurality of neuromuscular signals recorded by the neuromuscular sensors during performance of the at least one gesture by the user.

Other embodiments are directed to a method of calibrating performance of one or more statistical models used to generate a musculoskeletal representation. The method comprises controlling presentation of instructions via a user interface to instruct the user to perform the at least one gesture, and updating at least one parameter of the one or more statistical models based, at least in part, on a plurality of neuromuscular signals recorded by a plurality of neuromuscular sensors during performance of the at least one gesture by the user.

Other embodiments are directed to a computer-readable medium encoded with a plurality of instructions that, when executed by at least one processor, perform a method. The method comprises controlling presentation of instructions via a user interface to instruct the user to perform the at least one gesture, and updating at least one parameter of the one or more statistical models based, at least in part, on a plurality of neuromuscular signals recorded by a plurality of neuromuscular sensors during performance of the at least one gesture by the user.

Other embodiments are directed to a computerized system configured to calibrate performance of one or more statistical models used to generate a musculoskeletal representation, the system comprising: a plurality of neuromuscular sensors configured to continuously record a plurality of neuromuscular signals, wherein the plurality of neuromuscular sensors are arranged on at least one wearable device; and at least one computer processor is programmed to: process at least some of the plurality of neuromuscular signals using a statistical model to generate the musculoskeletal representation; determine based, at least in part, on at least one aspect of the musculoskeletal representation, that calibration of the statistical model used to generate the musculoskeletal model is needed; initiate a calibration session in response to determining that calibration is needed; update a statistical model configuration based, at least in part, on a plurality of neuromuscular signals recorded by the plurality of neuromuscular sensors and ground-truth data representing position information and/or force information recorded during the calibration session, to produce an updated statistical model; process at least some of the plurality of neuromuscular signals using the updated statistical model to generate an updated musculoskeletal representation; determine, based, at least in part, on the at least one aspect of the updated musculoskeletal representation whether further calibration of the statistical model is needed; and end the calibration session in response to determining that further calibration is not needed.

In one aspect, updating the statistical model configuration comprises selecting a different statistical model to generate the updated musculoskeletal representation than the statistical model used to generate to the musculoskeletal representation.

Other embodiments are directed to a method of calibrating performance of one or more statistical models used to generate a musculoskeletal representation, the method comprising: instructing, via a user interface, a user to perform at least one gesture while wearing a wearable device having a plurality of neuromuscular sensors arranged thereon; controlling presentation of instructions via the user interface to instruct the user to perform the at least one gesture; updating at least one parameter of the one or more statistical models based, at least in part, on a plurality of neuromuscular signals recorded by the plurality of neuromuscular sensors during performance of the at least one gesture by the user; identifying, based on an output of the one or more statistical models, a plurality of gesture characteristics that the one or more statistical model is poor at estimating; selecting a new gesture for the user to perform that includes the identified plurality of gesture characteristics; controlling presentation of instructions via the user interface to instruct the user to perform the new gesture; and updating at least one parameter of the one or more statistical models based, at least in part, on the plurality of neuromuscular signals recorded by the neuromuscular sensors during performance of the new gesture by the user.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

Various non-limiting embodiments of the technology will be described with reference to the following figures. It should be appreciated that the figures are not necessarily drawn to scale.

FIG. 7A illustrates a wearable portion of the computer-based system and FIG. 7B illustrates a dongle portion connected to a computer, wherein the dongle portion is configured to communicate with the wearable portion.

DETAILED DESCRIPTION

Figure 1:
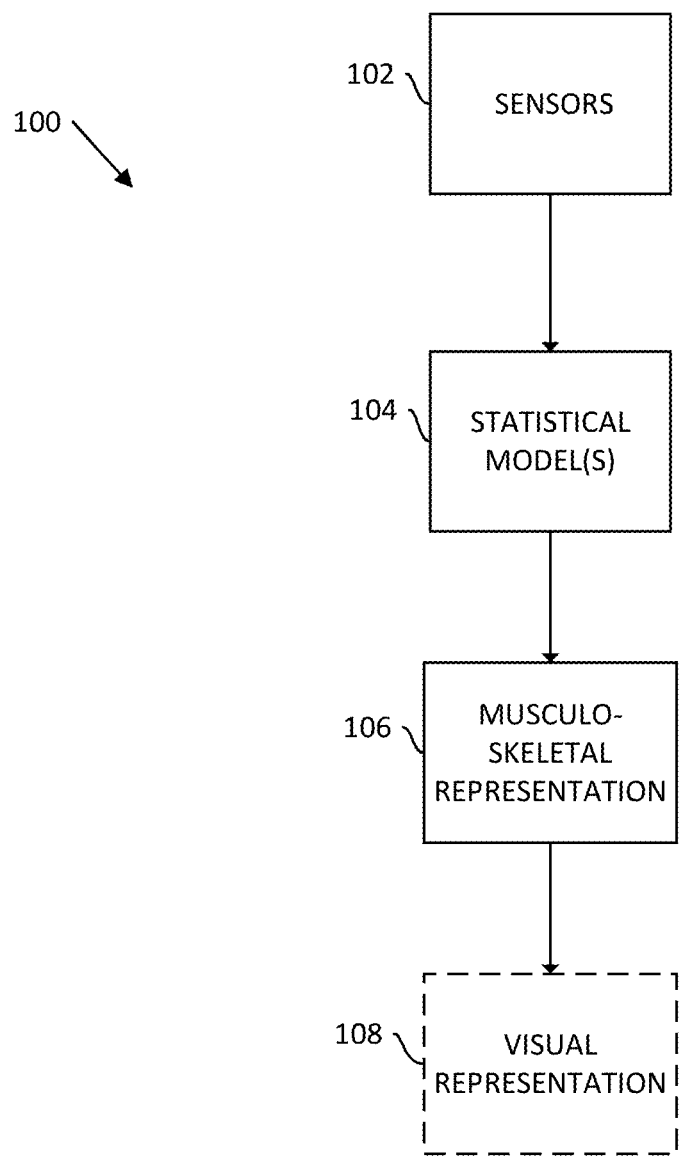
FIG. 1 is a schematic diagram of a computer-based system for generating a musculoskeletal representation based on neuromuscular sensor data in accordance with some embodiments of the technology described herein.

Robustness, consistency, and reliability are important features of a system for estimating the position, movement, and force exerted by a part of the human body, in part, because such features support realistic highly-immersive experiences in virtual environments and support the use of gesture-based machine control frameworks. Some conventional systems use neuromuscular signals to estimate the position and movement of a portion of a user's body represented as a multi-segment articulated rigid body system (e.g., a user's arm, hand, leg, etc.) in an autonomous manner. System calibration is typically performed in such systems using a sequence of prescribed movements or by changing the gain of signal amplification circuitry, though these systems generally have limited capabilities with respect to tuning, personalization, and retraining.

Some conventional camera-based systems for tracking a user's hand perform system calibration by calibrating imaging sensors or by configuring the system to distinguish individual users. Camera-based systems have some limitations relative to systems that use neuromuscular sensors to infer the position or movement of a part of the body, particularly with regard to occlusion and limited spatial functionality for fixed-camera based systems.

Neuromuscular signals contain information about motor-unit activity levels which determine the movements of joints and exerted forces. The degree to which estimates of joint angles and exerted forces generalize across users is limited by, variability between people with regard to characteristics such as joint stiffness, joint segment moments and inertia, and the relationship between motor unit activity and joint torque. When variations in such characteristics are not taken into consideration when predicting estimates of joint angles and forces from neuromuscular data, the models used to make the predictions may perform sub-optimally. To this end, some embodiments are directed to techniques for tuning model parameters based on neuromuscular data collected during a calibration procedure to account for user-specific physiological and anatomical differences.

All or portions of the human musculoskeletal system can be logically represented in a model implemented in a multi-segment articulated rigid body system. Such a model may be partitioned into multiple data structures including segments, logical interfaces, and other suitable data structures which, in ensemble, emulate biological functions and properties of the human musculoskeletal system. For instance, segments can represent rigid parts of the musculoskeletal system and logical interfaces can represent joints of the musculoskeletal system. Each of the data structures (e.g., segments and logical interfaces) can include attributes (variable and constant) denoting properties of the biological part that such data structure represents. As described in more detail below, the multi-segment articulated rigid body system may be configured to emulate biological functions and properties of the human musculoskeletal system.

All or portions of the human musculoskeletal system can be modeled as a multi-segment articulated rigid body system, with joint interfaces between different segments and joint angles defining the spatial relationships between connected segments in the model. Constraints on the movement at the joints are governed by the type of joint connecting the segments and the biological structures (e.g., muscles, tendons, ligaments, and other biological structures) that restrict the range of movement at the joint. For example, the shoulder joint connecting the upper arm to the torso and the hip joint connecting the upper leg to the torso are ball and socket joints that permit extension and flexion movements as well as rotational movements. By contrast, the elbow joint connecting the upper arm and the forearm and the knee joint connecting the upper leg and the lower leg allow for a more limited range of motion. As described herein, the multi-segment articulated rigid body system can be used to model portions of the human musculoskeletal system. Some segments of the human musculoskeletal system (e.g., the forearm segment), though approximated as a rigid body in the articulated rigid body system, may include multiple rigid structures (e.g., the ulna and radius bones of the forearm) that provide for more complex movement within the segment that is not explicitly considered by the rigid body model. Accordingly, a model of an articulated rigid body system for use with some embodiments of the technology described herein may include segments that represent a combination of body parts that are not strictly rigid bodies.

In kinematics, rigid bodies are objects that exhibit various attributes of motion (e.g., position, orientation, angular velocity, acceleration). Knowing the motion attributes of one segment of the rigid body enables the motion attributes for other segments of the rigid body to be determined based on constraints in how the segments are connected. For example, a hand can be modeled as a multi-segment articulated body with the joints in the wrist and each finger forming the interfaces between the multiple segments in the model. Movements of the segments in the rigid body model can be emulated as an articulated rigid body system in which position (e.g., actual position, relative position, or orientation) information of a segment relative to other segments in the model are predicted using a trained statistical model, as described in more detail below.

In some implementations, the multi-segment articulated rigid body system emulates portions of the human body, for example, a hand or a combination of a hand with one or more portions of an arm. Information used to describe position relationships between segments and force relationships for individual segments or combinations of segments in the musculoskeletal representation is referred to herein as the handstate of the musculoskeletal representation. The techniques described herein are also applicable to musculoskeletal representations of portions of the body other than the hand including, but not limited to, an arm, a leg, a foot, a torso, a neck, or any combination of the foregoing.

In addition to spatial information (e.g., position and orientation), in some implementations the multi-segment articulated rigid body system is configured to predict force information associated with one or more segments of the musculoskeletal representation. For example, the multi-segment articulated rigid body system can compute linear forces or rotational (torque) forces exerted by one or more segments. Examples of linear forces include, but are not limited to, the force of a finger or hand pressing on a solid object such as a table, and a force exerted when two segments (e.g., two fingers) are pinched together. Examples of rotational forces include, but are not limited to, rotational forces created when segments in the wrist or fingers are twisted or flexed.

In some implementations, a handstate can further include force information determined as a portion of a current handstate estimate that includes one or more of pinching force information, grasping force information, or information about co-contraction forces between muscles represented by the musculoskeletal representation.

FIG. 1 illustrates a system 100 in accordance with some embodiments. The system includes a plurality of sensors 102 configured to record signals resulting from the movement of portions of a human body. Sensors 102 may include autonomous sensors. As used herein, the term "autonomous sensors" refers to sensors configured to measure the movement of body segments without requiring the use of external devices. In some embodiments, sensors 102 may also include one or more auxiliary (e.g., non-autonomous) sensors in combination with autonomous sensors. Non-limiting examples of auxiliary sensors include, but are not limited to, wearable (e.g. body-mounted) cameras, global positioning systems, or laser scanning systems.

Autonomous sensors may include a plurality of neuromuscular sensors configured to record signals arising from neuromuscular activity in skeletal muscle of a human body. The term "neuromuscular activity" as used herein refers to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type that are configured to detect neuromuscular signals. In some embodiments, the plurality of neuromuscular sensors may be used to sense muscular activity related to a movement of the part of the body controlled by muscles from which the neuromuscular sensors are arranged to sense the muscle activity. Spatial information (e.g., position and/or orientation information) and force information describing the movement may be predicted based on the sensed neuromuscular signals as the user moves over time.

Autonomous sensors may include one or more Inertial Measurement Units (IMUs), which measure a combination of physical aspects of motion, using, for example, an accelerometer, a gyroscope, a magnetometer, or any combination of one or more accelerometers, gyroscopes and magnetometers. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect movements of one or more body segments distal to the torso (e.g., a forearm or wrist). It should be appreciated, however, that autonomous sensors may be arranged in any suitable way, and embodiments of the technology described herein are not limited based on the particular sensor arrangement. For example, in some embodiments, at least one IMU and a plurality of neuromuscular sensors may be co-located on a body segment to track movements of body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine movement information associated with wrist or hand segments to determine, for example, whether the user has an open or closed hand configuration.

Each of the autonomous sensors includes one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, the output of one or more of the sensing components may be processed using hardware signal processing circuitry (e.g., to perform amplification, filtering, and/or rectification). In other embodiments, at least some signal processing of the output of the sensing components may be performed in software. Thus, signal processing of autonomous signals recorded by the autonomous sensors may be performed in hardware, software, or by any suitable combination of hardware and software, as aspects of the technology described herein are not limited in this respect.

In some embodiments, the recorded sensor data may be processed to compute additional derived measurements that are then provided as input to a statistical model, as described in more detail below. For example, recorded signals from an IMU sensor may be processed to derive an orientation signal that specifies the orientation of a rigid body segment over time. Autonomous sensors may implement signal processing using components integrated with the sensing components, or at least a portion of the signal processing may be performed by one or more components in communication with, but not directly integrated with the sensing components of the autonomous sensors.

In some embodiments, at least some of the plurality of autonomous sensors are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the autonomous sensors may be arranged on a wearable patch configured to be affixed to a portion of the user's body. In some embodiments, multiple wearable devices, each having one or more IMUs and/or neuromuscular sensors included thereon may be used to predict musculoskeletal position information for movements that involve multiple parts of the body.

In some embodiments, sensors 102 only includes a plurality of neuromuscular sensors (e.g., EMG sensors). In other embodiments, sensors 102 includes a plurality of neuromuscular sensors and at least one "auxiliary" sensor configured to continuously record a plurality of auxiliary signals. Examples of auxiliary sensors include, but are not limited to, other autonomous sensors such as IMU sensors, and auxiliary sensors such as an imaging device (e.g., a camera), a radiation-based sensor for use with a radiation-generation device (e.g., a laser-scanning device), or other types of sensors such as a heart-rate monitor.

System 100 also includes one or more computer processors programmed to communicate with sensors 102. For example, signals recorded by one or more of the sensors may be provided to the processor(s), which may be programmed to execute one or more machine learning algorithms that process signals output by the sensors 102 to train one or more statistical models 104, and the trained (or retrained) statistical model(s) 104 may be stored for later use in generating a musculoskeletal representation 106, as described in more detail below.

In some embodiments, the statistical model may be implemented using one or more neural networks. Such neural network(s) may be implemented as one or more recurrent neural networks. For example, in some embodiments, the recurrent neural network may be a fully recurrent neural network, a recursive neural network, a variational autoencoder, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

The neural network(s) used in accordance with some embodiments may be implemented based on a variety of topologies and/or architectures including deep neural networks with fully connected (dense) layers, Long Short-Term Memory (LSTM) layers, convolutional layers, Temporal Convolutional Layers (TCL), or other suitable type of deep neural network topology and/or architecture. The neural network(s) may have different types of output layers including output layers with logistic sigmoid activation functions, hyperbolic tangent activation functions, linear units, rectified linear units, or other suitable type of nonlinear unit. Additionally, the neural network(s) may be configured to represent the probability distribution over n different classes via, for example, a softmax function or include an output layer that provides a parameterized distribution e.g., mean and variance of a Gaussian distribution. Other non-limiting examples of statistical models that may be used in accordance with some embodiments to predict handstate information based on recorded signals from sensors 102 are discussed in more detail below in connection with FIG. 5.

System 100 also optionally includes a display controller configured to display a visual representation 108 (e.g., of a hand). As discussed in more detail below, one or more computer processors may implement one or more trained statistical models configured to predict handstate information based, at least in part, on signals recorded by sensors 102. The predicted handstate information is used to update the musculoskeletal representation 106, which is then optionally used to render a visual representation 108 based on the updated musculoskeletal representation incorporating the current handstate information. Real-time reconstruction of the current handstate and subsequent rendering of the visual representation reflecting the current handstate information in the musculoskeletal model may provide visual feedback to the user about the effectiveness of the trained statistical model to accurately represent an intended handstate. Not all embodiments of system 100 include components configured to render a visual representation. For example, in some embodiments, handstate estimates output from the trained statistical model and a corresponding updated musculoskeletal representation are used to determine a state of a user's hand (e.g., in a virtual reality environment) even though a visual representation based on the updated musculoskeletal representation is not rendered.

In some embodiments, a computer application configured to simulate a virtual reality environment may be instructed to display a visual representation of the user's hand. Positioning, movement, and/or forces applied by portions of the hand within the virtual reality environment may be displayed based on the output of the trained statistical model(s). The visual representation may be dynamically updated based on current reconstructed handstate information as continuous signals are recorded by the sensors 102 and processed by the trained statistical model(s) 104 to provide an updated computer-generated representation of the user's position, movement, and/or force that is updated in real-time.

As discussed above, some embodiments are directed to using a statistical model for predicting musculoskeletal information based on signals recorded from wearable autonomous sensors. The statistical model may be used to predict the musculoskeletal position information without having to place sensors on each segment of the rigid body that is to be represented in the computer-generated musculoskeletal representation. As discussed briefly above, the types of joints between segments in a multi-segment articulated rigid body model constrain movement of the rigid body. Additionally, different individuals tend to move in characteristic ways when performing a task that can be captured in statistical patterns of individual user behavior. At least some of these constraints on human body movement may be explicitly incorporated into statistical models used for prediction in accordance with some embodiments. Additionally or alternatively, the constraints may be learned by the statistical model though training based on recorded sensor data. Constraints imposed in the construction of the statistical model are those set by anatomy and the physics of a user's body, while constraints derived from statistical patterns are those set by human behavior for one or more users from which sensor measurements are measured. The constraints may comprise part of the statistical model itself being represented by information (e.g., connection weights between nodes) in the model.

As discussed above, some embodiments are directed to using a statistical model for predicting handstate information to enable the generation and/or real-time update of a computer-based musculoskeletal representation. The statistical model may be used to predict the handstate information based on IMU signals, neuromuscular signals (e.g., EMG, MMG, and SMG signals), external device signals (e.g., camera or laser-scanning signals), or a combination of IMU signals, neuromuscular signals, and external device signals detected as a user performs one or more movements.

As described above, statistical models that predict estimates (e.g., handstate estimates) for updating a musculoskeletal representation include some constraints imposed in the construction of the statistical model set by anatomy and physics of a user's body and other constraints derived from statistical patterns set by human behavior for one or more users from which sensor measurements are measured. The constraints derived from statistical patterns set by human behavior may be initially learned by a statistical model by training the model using training data collected from a plurality of users to produce a user-independent model. Such a user-independent model may perform well in estimating position and/or force information (e.g., handstate estimates) based on recorded neuromuscular signals for some (e.g., simple) gestures, and may perform poorly in estimating such information for other (e.g., complex) gestures. To improve user-specific performance of the model, one or more parameters of the user-independent model may be updated based on user-specific data. Updating parameter(s) of a statistical model for a particular user and/or for usage during a particular recording session is referred to herein as "calibration" of the model performance.

Figure 2:
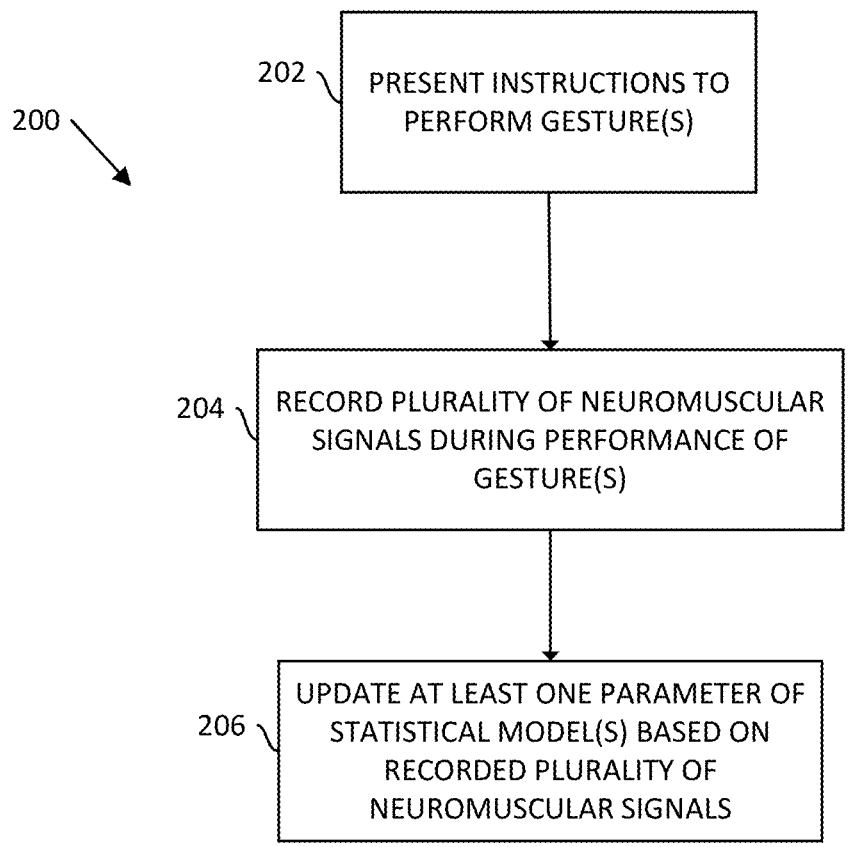
FIG. 2 is a flowchart of an illustrative process for calibrating performance of one or more statistical models in accordance of some embodiments of the technology described herein.

FIG. 2 illustrates a process 200 for calibrating performance of a statistical model that may be used in accordance with system 100, described in connection with FIG. 1. In some embodiments, the performance of one or more statistical models is calibrated by presenting the user with explicit instructions to perform one or more gestures. For example, the system may include a user interface configured to present instructions to the user to perform one or more gestures while wearing a wearable device on which a plurality of neuromuscular sensors are arranged and configured to record a plurality of neuromuscular signals. The user interface may be a visual interface, an audio interface, or any other suitable type of user interface for presenting the instructions to the user for performing one or more gestures. When the user interface is a visual interface, the instructions may be presented using text, static visual representations (e.g., images), dynamic visual representations (e.g., videos, animations), or any combination of the foregoing.

As used herein, the term "gestures" refers to a static or dynamic configuration of one or more body parts including the position of the one or more body parts and forces associated with the configuration. For example, gestures include discrete gestures, such as pressing the palm of a hand down on a solid surface or grasping a ball, continuous gestures, such as a waving a finger back and forth or throwing a ball, or a combination of discrete and continuous gestures such as grasping and throwing a ball. Gestures may be defined by an application configured to prompt a user to perform the gestures or, alternatively, gestures may be arbitrarily defined by a user.

After instructions are presented to the user to perform one or more gestures, process 200 proceeds to act 204, where a plurality of neuromuscular signals are recorded by a plurality of neuromuscular sensors arranged on the body of a user during performance of the gesture(s) in accordance with the presented instructions. As discussed above, the plurality of neuromuscular sensors may be arranged on one or wearable devices configured to be worn by a user during performance of one or more gestures. Process 200 then proceeds to act 206, where the statistical model configuration used to generate a musculoskeletal representation is updated based on the recorded plurality of neuromuscular signals. For example, in some embodiments, the statistical model configuration may be updated by selecting a different statistical model used to generate the musculoskeletal model. In other embodiments, at least one parameter of a statistical model may be updated based on the recorded plurality of neuromuscular signals. The one or more parameters of the statistical model may be updated in any suitable way. In some embodiments, one or more parameters of the statistical model may be updated by training the statistical model based, at least in part, on the recorded neuromuscular signals. In other embodiments, the one or more parameters of the statistical model may be updated without training or re-training the model. For example, the statistical model may receive as input the one or more parameters and updating the one or more parameters may comprise providing different values of the one or more parameters as input to the model. In yet further embodiments, the statistical model may be characterized by one or more parameters that are not provided as input to the model, but are nonetheless configurable, such that the parameter(s) may be updated based on neuromuscular signals recorded during performance of a gesture. For example, the configurable parameters may include a scaling factor by which recorded neuromuscular signals are scaled prior to being provided as input to the model.

Figure 3:
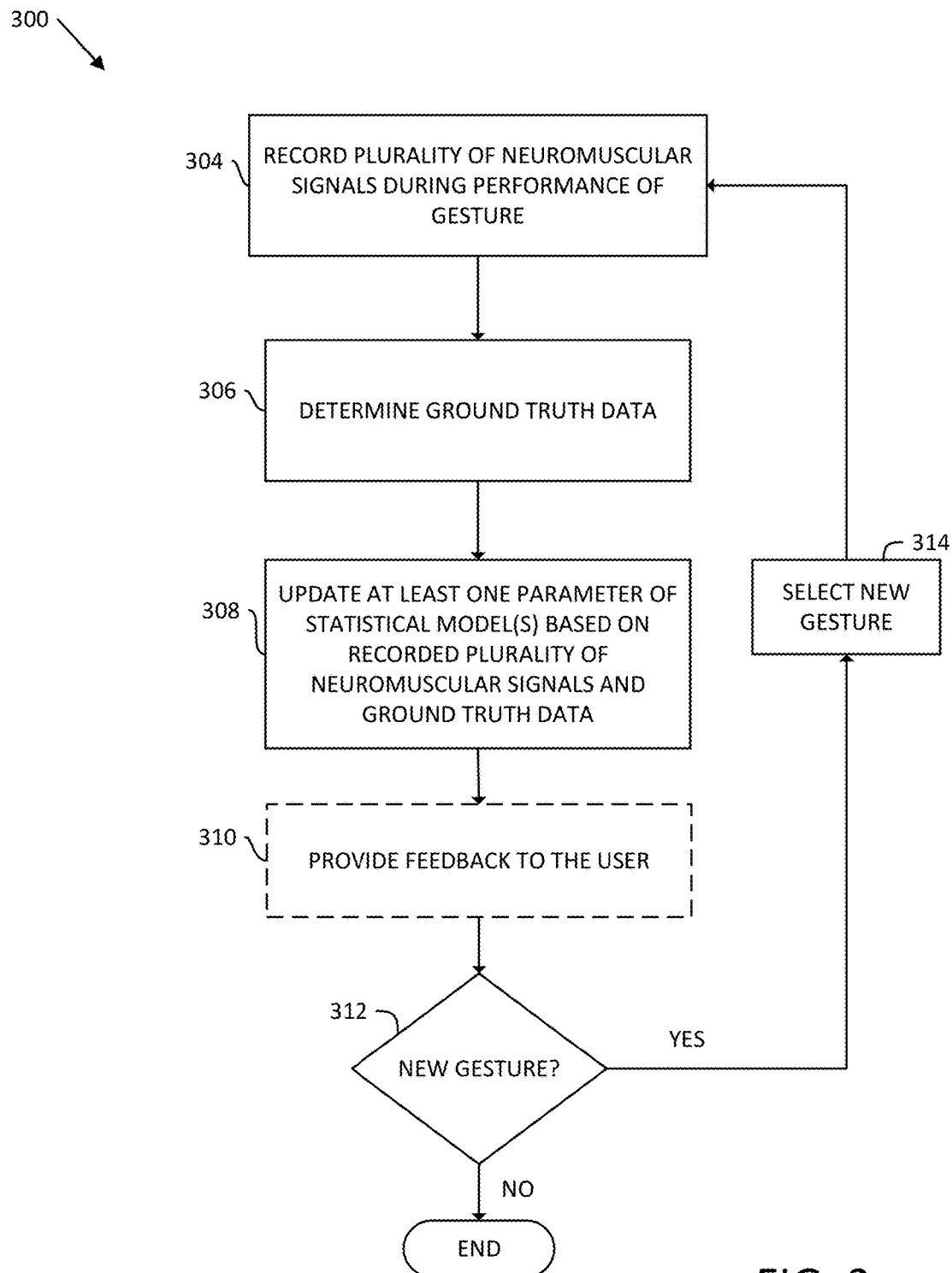
FIG. 3 is a flowchart of an illustrative process for calibrating performance of a statistical model in accordance with some embodiments of the technology described herein.

FIG. 3 illustrates a process 300 for updating one or more parameters of a statistical model in accordance with some embodiments. In act 304, a plurality of neuromuscular signals are recorded during performance of a gesture. As described above in connection with process 200, the neuromuscular signals may be recorded in response to prompting the user to perform one or more gestures as part of a training or retraining protocol to train the model. For example, a user may be instructed to hold their fingers out, orient their wrist parallel to their arm (e.g., not flexed or extended), and move their wrist with an ulnar deviation (e.g., towards their pinky finger). Alternatively, the plurality of neuromuscular signals may be recorded during runtime usage of the system after the model has been trained, and the performance of the model to accurately predict estimates may be tracked and used to determine whether to perform "online" calibration of the model, as discussed in more detail below.

In embodiments where updating the at least one parameter of the statistical model involves training or retraining the model, ground truth data representing the expected estimates output from the model in response to particular inputs are determined in act 306. In the simplest case, the ground truth data may be predetermined and defined based on the particular gesture that the user is instructed to perform. For example, when the estimates output from the model are handstate estimates that include a set of joint angles and forces for a musculoskeletal representation associated with a hand, a gesture may be defined by a particular set of joint angles and forces. In such a situation, the ground truth data may be determined as the particular set of joint angles and forces that define the gesture. Additionally or alternatively, the ground truth data may be determined based on neuromuscular information for the gesture. For example, the gesture may be characterized by a generic neuromuscular signal shape which may be used, at least in part, to determine the ground truth data.

In other embodiments, the ground truth data may be determined by one or more measurements captured by one or more external devices, examples of which include imaging devices (e.g., cameras) and inertial measurement units (IMUs). For example, when the external device is an imaging device configured to capture images, the imaging device may be controlled to capture at least one image as the user performs the gesture as the neuromuscular signals are recorded, and the one or more measurements may be determined based on the captured image(s).

In some embodiments that determine ground truth data from external devices, multiple external devices are used to determine the ground truth data. For example, an IMU may be used to determine some position/orientation such as large joint angles in the arm and wrist and an imaging device may be used to capture other position/orientation information such as smaller joint angles in the fingers. Other combinations of external devices may alternatively be used to determine position and/or force information as ground truth data, and embodiments are not limited in this respect. When measurements from multiple external devices are used to determine the ground truth data, the measurements from the multiple devices may be combined in any suitable way, and the statistical model may be updated based on the combined measurements.

Process 300 then proceeds to act 308, where at least one parameter of the statistical model is updated based on the plurality of neuromuscular signals recorded in act 304 and the ground truth data determined in act 306. Non-limiting examples of updating parameter(s) of a statistical model are described above in connection with act 206 of process 200.

Process 300 then proceeds to act 310, where feedback is optionally presented to the user to provide the user with information about whether the user's performance of the gesture was performed correctly as instructed (when instructions are provided). The feedback may be provided audibly, visually, using haptic feedback, or using any combination of the foregoing. When presented visually, the feedback may be provided as a static or dynamic visual representation of the gesture performed by the user to enable the user to compare how the model interpreted the user's performance of the gesture. In some embodiments, the feedback may illustrate a comparison between how the model estimates the user's performance of the gesture and how the gesture was intended to be performed based on the instructions provided. The feedback may then be interpreted by the user to determine whether the gesture was performed correctly and/or whether the model predicted the handstate estimates correctly based on the performed gesture. When it is determined that the model estimates were not accurate for the performed gesture, acts 304-310 may be repeated until the system and/or the user is satisfied that the model output can be used to accurately represent the performed gesture.

Process 300 then proceeds to act 312, where it is determined whether the process should be repeated with a new gesture. When it is determined to repeat the process with a new gesture, process 300 proceeds to act 314 where a new gesture is selected. Otherwise, the process ends.

Determining whether acts 304-310 of process 300 should be repeated with a new gesture may be determined in any suitable way. In a passive calibration procedure, the user may be instructed to perform a predetermined set of gestures and determining whether to perform a new gesture may be determined based on whether all of the gestures in the set have been performed. This calibration procedure is referred to as "passive" herein as the gestures performed are not actively determined (e.g., based on the performance of the model), but are predetermined based on the gestures in the set. Passive calibration may be used, for example, when a user first uses the system to provide user-specific initial training of the statistical model or when the user uses the system to control a new application that associates particular gestures with control commands in the application. Passive calibration may be used to ensure that the statistical model is trained on a base set of uniform gestures relevant to a particular application. When using a passive calibration procedure, the gestures in the set may be selected in act 314 randomly from the set for performance by the user during calibration or the user may be instructed to perform at least some of the gestures in the set in a particular order. For example, the particular order may specify that the model be trained on simple gestures prior to training the model on more complex gestures.

As an alternative to passive calibration, some embodiments employ an active calibration procedure, where a new gesture to be performed is not determined based on a predetermined set of gestures, but instead selection of a new gesture is informed based on performance of the model. In an active calibration procedure, new gestures to perform are actively suggested to the user based on an online (e.g., Bayesian) estimation of the model performance. For example, it may be determined that the model performs well for estimating certain gesture characteristics but performs poorly for estimating other gesture characteristics. As discussed above, each gesture may be defined by a plurality of gesture characteristics (e.g., joint angles and forces), and the gesture that is selected during an active calibration procedure may be selected based on the gesture characteristic(s) that the model estimates poorly and gestures that include the gesture characteristic(s).

In some implementations of an active calibration procedure, a new gesture may be selected randomly from a set of gestures having gesture characteristics which the model estimates poorly. In other implementations of an active calibration procedure, a new gesture to be performed by the user may be selected as a gesture previously performed by the user, but on which performance of the model is poorly calibrated. In yet further implementations of an active calibration procedure, a new gesture is selected based, at least in part, on whether the particular gesture is defined by multiple gesture characteristics that the model estimates poorly. In some embodiments, a gesture that includes a maximum number of gesture characteristics for which the model performs poorly may be selected.

When either a passive calibration procedure or an active calibration procedure is used, the user may be provided with explicit instructions explaining the gesture to be performed by, for example, displaying on a user interface a static or dynamic visual representation of the gesture to be performed. Alternatively, the instructions provided to the user may include at least one user-interpretable instruction that may be subjectively interpreted by the user to perform the gesture. In such a procedure, the user actively participates in the calibration by determining, at least in part, how to perform the gesture. As an example, the user may be provided with a series of prompts that instructs the user to pinch two fingers at different percentages (e.g., 25%, 50%, 75%, 100%) of force exerted between the fingers relative to the maximum exertion. Using such a technique, the user defines how a percentage of maximal force maps to the neuromuscular signals recorded during performance of the gesture. Other examples of user-interpretable instruction include, but are not limited to, moving a slider along a bar or line, interacting (e.g., clenching) with an object, and pressing against a surface.

As discussed above, in connection with act 310 of process 300, feedback may be provided to a user during a passive or active calibration procedure when user-interpretable instructions are included. The feedback may include rendering a visual representation associated with a hand. Additionally, in some embodiments, the visual representation may include force metrics to provide feedback on exerted forces to the user. Force metrics may be provided to the user in any suitable way, examples of which include, but are not limited to, using different colors, bar plots, scatterplots, time series plots, etc. In some embodiments, metrics in addition to or as an alternative to force metrics may also be provided as feedback to a user. For example, additional metrics may include the extent to which the gesture is completed or the degree to which the gesture is completed (e.g., 50% completed), metrics describing whether the completed or partially-completed gesture is accurate, or any other suitable metrics that provide feedback to the user as the user is performing the gesture may be provided.

As discussed briefly above, the calibration procedures described herein may be performed at different times. For example, training or retraining the model may occur prior to use of the system by a new user and/or for a new application. Such calibration individualizes the statistical model(s) based on user-specific physiological and/or anatomical characteristics. Additionally or alternatively, the calibration procedures may be performed as the user is using the system.

Figure 4:
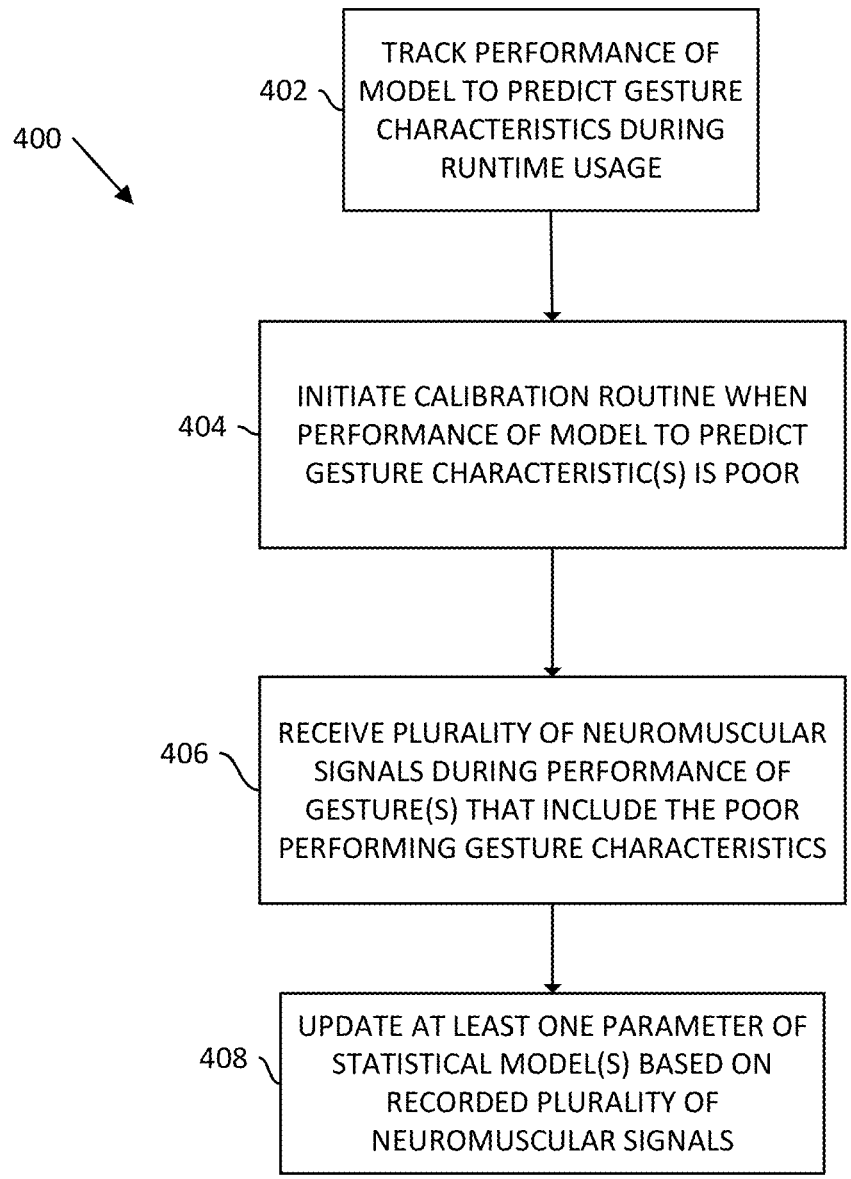
FIG. 4 is a flowchart of an illustrative process for initiating a calibration routine to update parameters of a trained statistical model during runtime in accordance with some embodiments of the technology described herein.

FIG. 4 illustrates a process 400 for performing calibration during normal use of the system. In act 402, the performance of the model is tracked to predict the performance of the model in accurately predicting gestures and/or gesture characteristics during runtime. When it is determined that the model should be calibrated based on reduced model performance for one or more gestures or gesture characteristics, process 400 proceeds to act 404, where a calibration routine is initiated. The determination to initiate a calibration routine may be made in any suitable way. For example, one or more quality measures may be determined for model estimates corresponding to gestures or gesture characteristics and it may be determined to initiate a calibration routine when the quality measure(s) fall below a threshold for the gestures/gesture characteristics. In one non-limiting example, a calibration routine may be initiated if the probabilities among several possible gestures exhibits relatively high entropy. In contrast, a well-calibrated statistical model may calculate the likelihood of one gesture to be high (e.g., greater than 0.8, greater than 0.9, close to 1) and the posterior probabilities for other gestures to be small. In another example, if the model frequently identifies gestures with low likelihood (generally indicating the presence or estimation of many 'long tail' gestures), a calibration routine may be initiated or a user notification may be presented to the user to determine whether the user was in fact initiating uncommon hand gestures.

In some cases, a calibration routine may be used to account for a user's anatomy. For example, a detector circuit may be configured to detect whether a user has the palmaris longus muscle in their arm. One way to determine if a user has a palmaris longus muscle is to instruct the user to pinch the fingertips of their pinky and thumb while flexing their wrist. In response to a determination that the user does have the palmaris longus muscle in their arm, an appropriate calibration routine may be initiated that is specifically configured to calibrate for individuals with a palmar longus muscle. In another example, a calibration routine may be initiated to account for the effect of a user's anatomy on the conductive profile of the user's body (e.g., their arm). One factor that affects the conduction of electrical currents in the body is the location and amount of adipose tissue in the arm. Adipose tissue affects the filtering of neuromuscular activity recorded by electromyography at the skin surface, so a calibration routine optimized for improving a statistical model based on the location and amount of adipose tissue may be initiated. One skilled in the art will recognize that the location and amount of adipose tissue in a user may be measured or estimated in various ways, including via ultrasonography. In another example, the effect of a particular muscle activation on the movement of a part of the body (e.g., the hand) depends on individual anatomy, including the size of the arm or hand and properties of the user's joints (e.g., joint stiffness, joint segment moments and inertia, and the relationship between motor unit activity and joint torque), and variations in individual anatomy that affect how joints move based on a given muscle activation may cause degraded model performance and cause a calibration routine to be initiated.

Initiation of a calibration routine may be made apparent to the user by, for example, the system entering a "calibration mode" where the user is prompted with instructions to perform one or more gestures to calibrate performance of the model, as discussed above. Halting usage of the system and entering a calibration mode may enable the model performance to improve quickly by having the user focus on performing gestures with characteristics that the model estimates poorly.

Alternatively, initiation of a calibration routine may occur during routine usage of the system without the user becoming aware that calibration is being performed. For example, the system may identify gestures and/or gesture characteristics for which model calibration is desired, and when gestures/gesture characteristics are performed by the user during ordinary usage of the system, calibration may be performed using neuromuscular signals recorded during performance of such gestures. By not making the calibration procedure apparent to the user, the user's use of the system is not interrupted, and the model adapts through normal use of the system.

After initiating a calibration routine, process 400 proceeds to act 406, where a plurality of neuromuscular signals are recorded during performance of gestures that include the identified gesture characteristic(s) on which the model performs poorly. Process 400 then proceeds to act 408, where at least one parameter of the model is updated based on the recorded plurality of neuromuscular signals. As discussed above, updating the parameter(s) of a statistical model may be implemented by training/retraining the model, modifying inputs to the model or changing other configurable parameters of the model. In some embodiments, some simple updates to the parameter(s) of the model may occur during runtime usage of the model, whereas more complex updates (e.g., retraining the model) may occur offline when the system is not being used by the user. When the model updates happen is not a limitation of the technology described herein.

Some model parameters, examples of which include, but are not limited to, a user's muscular anatomical features, a location of single muscles, muscle gain, and joint stiffness, are not expected to change substantially from session to session. Such model parameters may be stored in a user profile for the user, and the user profile may be accessed each time the user uses the system in a new session. In some embodiments, a user's user profile is updated with each new calibration session, for example, to track a user's long-term changes in physiology and/or anatomy. Other model parameters may be both user dependent and session dependent. For example, the placement of the neuromuscular sensors on the user's body may change from session to session or may even change during a session resulting in varying model estimates. For example, the placement of neuromuscular sensors in an armband may be rotated circumferentially around the arm; the armband may be placed on the arm oriented to be facing either proximally or distally; the armband may be placed on a different arm relative to an earlier calibration session; or the armband may be shifted along the proximal-distal axis of the arm (e.g., closer to the hand or closer to the shoulder). In another example, a user may experience muscle fatigue during a session, causing the pattern of motor unit activation to change, and a calibration session may be useful to account for the changing pattern of motor unit activation. Model parameters relating to session-dependent events may need to be updated each session and as such, may not be stored in the user's profile. However, some session-dependent events may be characteristic of a user (e.g., propensity of a muscle to experience fatigue) and as such, may be stored in the user's profile. In some embodiments, a determination is made during or at the end of a session regarding which model parameter updates made during the session should persist and be stored in the user's profile and which model parameter updates made during the session are session dependent and should be discarded following the session. The determination may be made based on the type of update, examples of which are described above.

Figure 5:
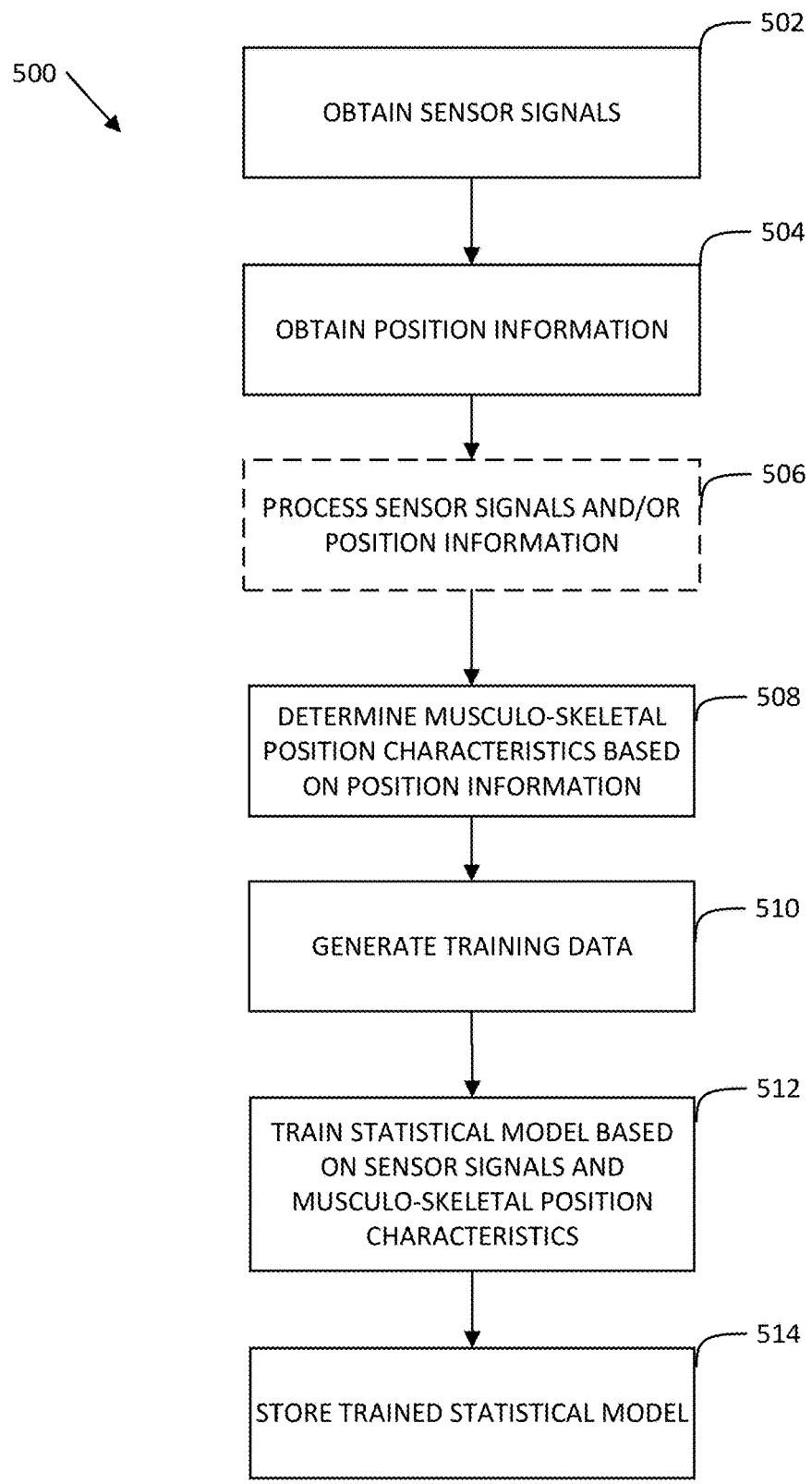
FIG. 5 is a flowchart of an illustrative process for generating a statistical model for predicting musculoskeletal position information using signals recorded from sensors, in accordance with some embodiments of the technology described herein.

FIG. 5 describes a process 500 for generating (sometimes termed "training" herein) a statistical model using signals recorded from sensors 102. Process 500 may be executed by any suitable computing device(s), as aspects of the technology described herein are not limited in this respect. For example, process 500 may be executed by one or more computer processors described with reference to FIGS. 7A and 7B. As another example, one or more acts of process 500 may be executed using one or more servers (e.g., servers included as a part of a cloud computing environment). For example, at least a portion of act 510 relating to training of a statistical model (e.g., a neural network) may be performed using a cloud computing environment.

Process 500 begins at act 502, where a plurality of sensor signals are obtained for one or multiple users performing one or more movements (e.g., typing on a keyboard). In some embodiments, the plurality of sensor signals may be recorded as part of process 500. In other embodiments, the plurality of sensor signals may have been recorded prior to the performance of process 500 and are accessed (rather than recorded) at act 502.

In some embodiments, the plurality of sensor signals may include sensor signals recorded for a single user performing a single movement or multiple movements. The user may be instructed to perform a sequence of movements for a particular task (e.g., opening a door) and sensor signals corresponding to the user's movements may be recorded as the user performs the task he/she was instructed to perform. The sensor signals may be recorded by any suitable number of sensors located in any suitable location(s) to detect the user's movements that are relevant to the task performed. For example, after a user is instructed to perform a task with the fingers of his/her right hand, the sensor signals may be recorded by multiple neuromuscular sensors circumferentially (or otherwise) arranged around the user's lower right arm to detect muscle activity in the lower right arm that give rise to the right hand movements and one or more IMU sensors arranged to predict the joint angle of the user's arm relative to the user's torso. As another example, after a user is instructed to perform a task with his/her leg (e.g., to kick an object), sensor signals may be recorded by multiple neuromuscular sensors circumferentially (or otherwise) arranged around the user's leg to detect muscle activity in the leg that give rise to the movements of the foot and one or more IMU sensors arranged to predict the joint angle of the user's leg relative to the user's torso.

In some embodiments, the sensor signals obtained in act 502 correspond to signals from one type of sensor (e.g., one or more IMU sensors or one or more neuromuscular sensors) and a statistical model may be trained based on the sensor signals recorded using the particular type of sensor, resulting in a sensor-type specific trained statistical model. For example, the obtained sensor signals may comprise a plurality of EMG sensor signals arranged around the lower arm or wrist of a user and the statistical model may be trained to predict musculoskeletal position information for movements of the wrist and/or hand during performance of a task such as grasping and twisting an object such as a doorknob.

In embodiments that provide predictions based on multiple types of sensors (e.g., IMU sensors, EMG sensors, MMG sensors, SMG sensors), a separate statistical model may be trained for each of the types of sensors and the outputs of the sensor-type specific models may be combined to generate a musculoskeletal representation of the user's body. In other embodiments, the sensor signals obtained in act 502 from two or more different types of sensors may be provided to a single statistical model that is trained based on the signals recorded from the different types of sensors. In one illustrative implementation, an IMU sensor and a plurality of EMG sensors are arranged on a wearable device configured to be worn around the forearm of a user, and signals recorded by the IMU and EMG sensors are collectively provided as inputs to a statistical model, as discussed in more detail below.

In some embodiments, the sensor signals obtained in act 502 are recorded at multiple time points as a user performs one or multiple movements. As a result, the recorded signal for each sensor may include data obtained at each of multiple time points. Assuming that n sensors are arranged to simultaneously measure the user's movement information during performance of a task, the recorded sensor signals for the user may comprise a time series of K n-dimensional vectors $\{x_k | 1 \leq k \leq K\}$ at time points $t_1, t_2, \ldots, t_K$ during performance of the movements.

In some embodiments, a user may be instructed to perform a task multiple times and the sensor signals and position information may be recorded for each of multiple repetitions of the task by the user. In some embodiments, the plurality of sensor signals may include signals recorded for multiple users, each of the multiple users performing the same task one or more times. Each of the multiple users may be instructed to perform the task and sensor signals and position information corresponding to that user's movements may be recorded as the user performs (once or repeatedly) the task he/she was instructed to perform. When sensor signals are collected by multiple users which are combined to generate a statistical model, an assumption is that different users employ similar musculoskeletal positions to perform the same movements. Collecting sensor signals and position information from a single user performing the same task repeatedly and/or from multiple users performing the same task one or multiple times facilitates the collection of sufficient training data to generate a statistical model that can accurately predict musculoskeletal position information associated with performance of the task.

In some embodiments, a user-independent statistical model may be generated based on training data corresponding to the recorded signals from multiple users, and as the system is used by a user, the statistical model is trained based on recorded sensor data such that the statistical model learns the user-dependent characteristics to refine the prediction capabilities of the system for the particular user.

In some embodiments, the plurality of sensor signals may include signals recorded for a user (or each of multiple users) performing each of multiple tasks one or multiple times. For example, a user may be instructed to perform each of multiple tasks (e.g., grasping an object, pushing an object, and pulling open a door) and signals corresponding to the user's movements may be recorded as the user performs each of the multiple tasks he/she was instructed to perform. Collecting such data may facilitate developing a statistical model for predicting musculoskeletal position information associated with multiple different actions that may be taken by the user. For example, training data that incorporates musculoskeletal position information for multiple actions may facilitate generating a statistical model for predicting which of multiple possible movements a user may be performing.

As discussed above, the sensor data obtained at act 502 may be obtained by recording sensor signals as each of one or multiple users performs each of one or more tasks one or more multiple times. As the user(s) perform the task(s), position information describing the spatial position of different body segments during performance of the task(s) may be obtained in act 504. In some embodiments, the position information is obtained using one or more external devices or systems that track the position of different points on the body during performance of a task. For example, a motion capture system, a laser scanner, a device to measure mutual magnetic induction, or some other system configured to capture position information may be used. As one non-limiting example, a plurality of position sensors may be placed on segments of the fingers of the right hand and a motion capture system may be used to determine the spatial location of each of the position sensors as the user performs a task such as grasping an object. The sensor data obtained at act 502 may be recorded simultaneously with recording of the position information obtained in act 504. In this example, position information indicating the position of each finger segment over time as the grasping motion is performed is obtained.

Next, process 500 proceeds to act 506, where the sensor signals obtained in act 502 and/or the position information obtained in act 504 are optionally processed. For example, the sensor signals or the position information signals may be processed using amplification, filtering, rectification, or other types of signal processing.

Next, process 500 proceeds to act 508, where musculoskeletal position characteristics are determined based on the position information (as collected in act 504 or as processed in act 506). In some embodiments, rather than using recorded spatial (e.g., x, y, z) coordinates corresponding to the position sensors as training data to train the statistical model, a set of derived musculoskeletal position characteristic values are determined based on the recorded position information, and the derived values are used as training data for training the statistical model. For example, using information about the constraints between connected pairs of rigid segments in the articulated rigid body model, the position information may be used to determine joint angles that define angles between each connected pair of rigid segments at each of multiple time points during performance of a task. Accordingly, the position information obtained in act 504 may be represented by a vector of n joint angles at each of a plurality of time points, where n is the number of joints or connections between segments in the articulated rigid body model.

Next, process 500 proceeds to act 510, where the time series information obtained at acts 502 and 508 is combined to create training data used for training a statistical model at act 510. The obtained data may be combined in any suitable way. In some embodiments, each of the sensor signals obtained at act 502 may be associated with a task or movement within a task corresponding to the musculoskeletal position characteristics (e.g., joint angles) determined based on the positional information recorded in act 504 as the user performed the task or movement. In this way, the sensor signals may be associated with musculoskeletal position characteristics (e.g., joint angles) and the statistical model may be trained to predict that the musculoskeletal representation will be characterized by particular musculoskeletal position characteristics between different body segments when particular sensor signals are recorded during performance of a particular task.

In embodiments comprising sensors of different types (e.g., IMU sensors and neuromuscular sensors) configured to simultaneously record different types of movement information during performance of a task, the sensor data for the different types of sensors may be recorded using the same or different sampling rates. When the sensor data is recorded at different sampling rates, at least some of the sensor data may be resampled (e.g., up-sampled or down-sampled) such that all sensor data provided as input to the statistical model corresponds to time series data at the same time resolution. Resampling at least some of the sensor data may be performed in any suitable way including, but not limited to using interpolation for upsampling and using decimation for downsampling.

In addition to or as an alternative to resampling at least some of the sensor data when recorded at different sampling rates, some embodiments employ a statistical model configured to accept multiple inputs asynchronously. For example, the statistical model may be configured to model the distribution of the "missing" values in the input data having a lower sampling rate. Alternatively, the timing of training of the statistical model occur asynchronously as input from multiple sensor data measurements becomes available as training data.

Next, process 500 proceeds to act 512, where a statistical model for predicting musculoskeletal position information is trained using the training data generated at act 510. The statistical model being trained may take as input a sequence of data sets each of the data sets in the sequence comprising an n-dimensional vector of sensor data. The statistical model may provide output that indicates, for each of one or more tasks or movements that may be performed by a user, the likelihood that the musculoskeletal representation of the user's body will be characterized by a set of musculoskeletal position characteristics (e.g., a set of joint angles between segments in an articulated multi-segment body model). For example, the statistical model may take as input a sequence of vectors $\{x_k | 1 \leq k \leq K\}$ generated using measurements obtained at time points $t_1, t_2, \ldots, t_K$, where the ith component of vector $x_j$ is a value measured by the ith sensor at time $t_j$ and/or derived from the value measured by the ith sensor at time $t_j$. In another non-limiting example, a derived value provided as input to the statistical model may comprise features extracted from the data from all or a subset of the sensors at and/or prior to time $t_j$ (e.g., a covariance matrix, a power spectrum, a combination thereof, or any other suitable derived representation). Based on such input, the statistical model may provide output indicating, a probability that a musculoskeletal representation of the user's body will be characterized by a set of musculoskeletal position characteristics. As one non-limiting example, the statistical model may be trained to predict a set of joint angles for segments in the fingers in the hand over time as a user grasps an object. In this example, the trained statistical model may output, a set of predicted joint angles for joints in the hand corresponding to the sensor input.

In some embodiments, the statistical model may be a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be a fully recurrent neural network, a recursive neural network, a variational autoencoder, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

In some of the embodiments in which the statistical model is a neural network, the output layer of the neural network may provide a set of output values corresponding to a respective set of possible musculoskeletal position characteristics (e.g., joint angles). In this way, the neural network may operate as a non-linear regression model configured to predict musculoskeletal position characteristics from raw or pre-processed sensor measurements. It should be appreciated that, in some embodiments, any other suitable non-linear regression model may be used instead of a neural network, as aspects of the technology described herein are not limited in this respect.

In some embodiments, the neural network can be implemented based on a variety of topologies and/or architectures including deep neural networks with fully connected (dense) layers, Long Short-Term Memory (LSTM) layers, convolutional layers, Temporal Convolutional Layers (TCL), or other suitable type of deep neural network topology and/or architecture. The neural network can have different types of output layers including output layers with logistic sigmoid activation functions, hyperbolic tangent activation functions, linear units, rectified linear units, or other suitable type of nonlinear unit. Likewise, the neural network can be configured to represent the probability distribution over n different classes via, for example, a softmax function or include an output layer that provides a parameterized distribution e.g., mean and variance of a Gaussian distribution.

It should be appreciated that aspects of the technology described herein are not limited to using neural networks, as other types of statistical models may be employed in some embodiments. For example, in some embodiments, the statistical model may comprise a hidden Markov model, a Markov switching model with the switching allowing for toggling among different dynamic systems, dynamic Bayesian networks, and/or any other suitable graphical model having a temporal component. Any such statistical model may be trained at act 512 using the sensor data obtained at act 502.

As another example, in some embodiments, the statistical model may take as input, features derived from the sensor data obtained at act 502. In such embodiments, the statistical model may be trained at act 512 using features extracted from the sensor data obtained at act 502. The statistical model may be a support vector machine, a Gaussian mixture model, a regression based classifier, a decision tree classifier, a Bayesian classifier, and/or any other suitable classifier, as aspects of the technology described herein are not limited in this respect. Input features to be provided as training data to the statistical model may be derived from the sensor data obtained at act 502 in any suitable way. For example, the sensor data may be analyzed as time series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor data may be transformed using a wavelet transform and the resulting wavelet coefficients may be provided as inputs to the statistical model.

In some embodiments, at act 512, values for parameters of the statistical model may be estimated from the training data generated at act 510. For example, when the statistical model is a neural network, parameters of the neural network (e.g., weights) may be estimated from the training data. In some embodiments, parameters of the statistical model may be estimated using gradient descent, stochastic gradient descent, and/or any other suitable iterative optimization technique. In embodiments where the statistical model is a recurrent neural network (e.g., an LSTM), the statistical model may be trained using stochastic gradient descent and backpropagation through time. The training may employ a cross-entropy loss function and/or any other suitable loss function, as aspects of the technology described herein are not limited in this respect.

Next, process 500 proceeds to act 514, where the trained statistical model is stored (e.g., in datastore—not shown). The trained statistical model may be stored using any suitable format, as aspects of the technology described herein are not limited in this respect. In this way, the statistical model generated during execution of process 500 may be used at a later time, for example, to predict musculoskeletal position information (e.g., joint angles) for a given set of input sensor data, as described below.

In some embodiments, sensor signals are recorded from a plurality of sensors (e.g., arranged on or near the surface of a user's body) that record activity associated with movements of the body during performance of a task. The recorded signals may be optionally processed and provided as input to a statistical model trained using one or more techniques described above in connection with FIG. 5. In some embodiments that continuously record autonomous signals, the continuously recorded signals (raw or processed) may be continuously or periodically provided as input to the trained statistical model for prediction of musculoskeletal position information (e.g., joint angles) for the given set of input sensor data. As discussed above, in some embodiments, the trained statistical model is a user-independent model trained based on autonomous sensor and position information measurements from a plurality of users. In other embodiments, the trained model is a user-dependent model trained on data recorded from the individual user from which the data associated with the sensor signals is also acquired.

After the trained statistical model receives the sensor data as a set of input parameters, the predicted musculoskeletal position information is output from the trained statistical model. As discussed above, in some embodiments, the predicted musculoskeletal position information may comprise a set of musculoskeletal position information values (e.g., a set of joint angles) for a multi-segment articulated rigid body model representing at least a portion of the user's body. In other embodiments, the musculoskeletal position information may comprise a set of probabilities that the user is performing one or more movements from a set of possible movements.

In some embodiments, after musculoskeletal position information is predicted, a computer-based musculoskeletal representation of the user's body is generated based, at least in part, on the musculoskeletal position information output from the trained statistical model. The computer-based musculoskeletal representation may be generated in any suitable way. For example, a computer-based musculoskeletal model of the human body may include multiple rigid body segments, each of which corresponds to one or more skeletal structures in the body. For example, the upper arm may be represented by a first rigid body segment, the lower arm may be represented by a second rigid body segment the palm of the hand may be represented by a third rigid body segment, and each of the fingers on the hand may be represented by at least one rigid body segment (e.g., at least fourth-eighth rigid body segments). A set of joint angles between connected rigid body segments in the musculoskeletal model may define the orientation of each of the connected rigid body segments relative to each other and a reference frame, such as the torso of the body. As new sensor data is measured and processed by the statistical model to provide new predictions of the musculoskeletal position information (e.g., an updated set of joint angles), the computer-based musculoskeletal representation of the user's body may be updated based on the updated set of joint angles determined based on the output of the statistical model. In this way the computer-based musculoskeletal representation is dynamically updated in real-time as sensor data is continuously recorded.

The computer-based musculoskeletal representation may be represented and stored in any suitable way, as embodiments of the technology described herein are not limited with regard to the particular manner in which the representation is stored. Additionally, although referred to herein as a "musculoskeletal" representation, to reflect that muscle activity may be associated with the representation in some embodiments, as discussed in more detail below, it should be appreciated that some musculoskeletal representations used in accordance with some embodiments may correspond to skeletal structures, muscular structures or a combination of skeletal structures and muscular structures in the body.

In some embodiments, direct measurement of neuromuscular activity and/or muscle activity underlying the user's movements may be combined with the generated musculoskeletal representation. Measurements from a plurality of sensors placed at locations on a user's body may be used to create a unified representation of muscle recruitment by superimposing the measurements onto a dynamically-posed skeleton. In some embodiments, muscle activity sensed by neuromuscular sensors and/or information derived from the muscle activity (e.g., force information) may be combined with the computer-generated musculoskeletal representation in real time.

Figure 6A:
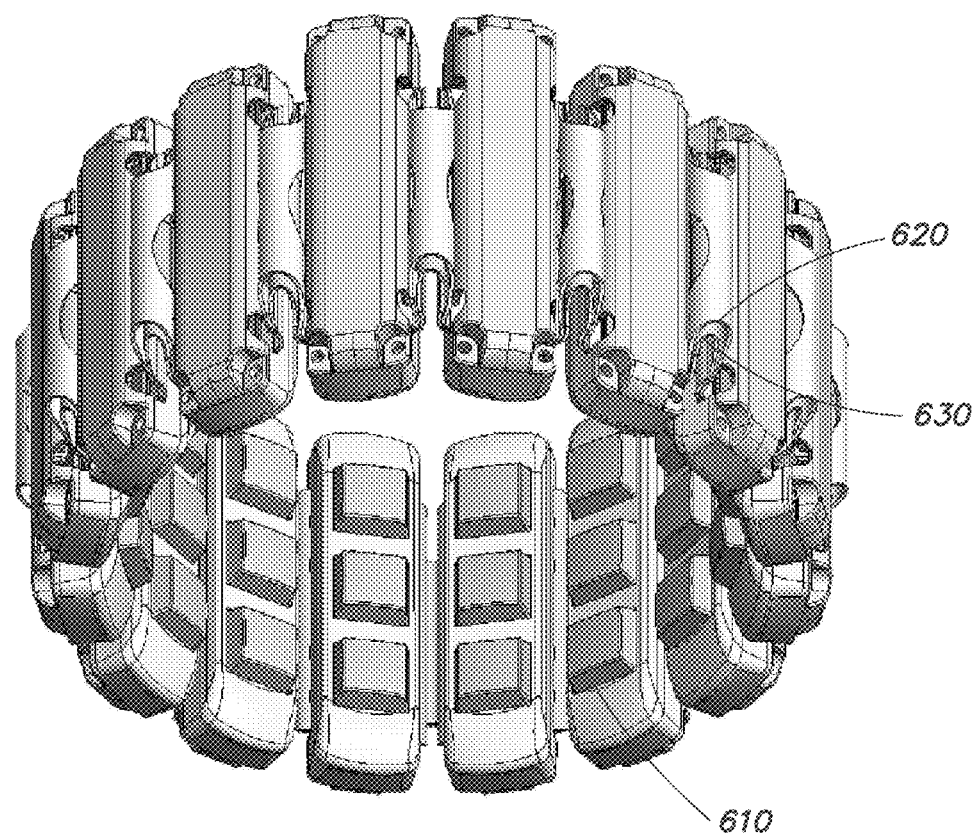
FIG. 6A illustrates a wearable system with sixteen EMG sensors arranged circumferentially around an elastic band configured to be worn around a user's lower arm or wrist, in accordance with some embodiments of the technology described herein.

FIG. 6A illustrates a wearable system with sixteen neuromuscular sensors 610 (e.g., EMG sensors) arranged circumferentially around an elastic band 620 configured to be worn around a user's lower arm or wrist. As shown, EMG sensors 610 are arranged circumferentially around elastic band 620. It should be appreciated that any suitable number of neuromuscular sensors may be used. The number and arrangement of neuromuscular sensors may depend on the particular application for which the wearable device is used. For example, a wearable armband or wristband can be used to generate control information for controlling an augmented reality system, a robot, controlling a vehicle, scrolling through text, controlling a virtual avatar, or any other suitable control task.

Figure 6B:
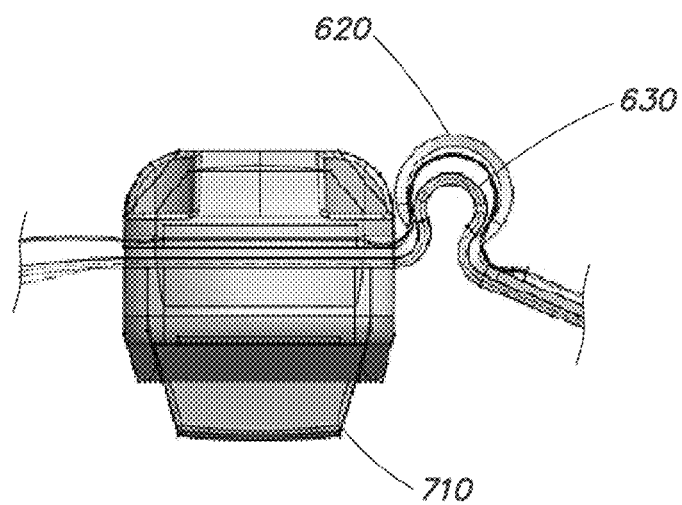
FIG. 6B is a cross-sectional view through one of the sixteen EMG sensors illustrated in FIG. 6A.

In some embodiments, sensors 610 includes a set of neuromuscular sensors (e.g., EMG sensors). In other embodiments, sensors 610 can include a set of neuromuscular sensors and at least one "auxiliary" sensor configured to continuously record auxiliary signals. Examples of auxiliary sensors include, but are not limited to, other sensors such as IMU sensors, microphones, imaging sensors (e.g., a camera), radiation based sensors for use with a radiation-generation device (e.g., a laser-scanning device), or other types of sensors such as a heart-rate monitor. As shown the sensors 610 may be coupled together using flexible electronics 630 incorporated into the wearable device. FIG. 6B illustrates a cross-sectional view through one of the sensors 610 of the wearable device shown in FIG. 6A.

Figures 7A, 7B:
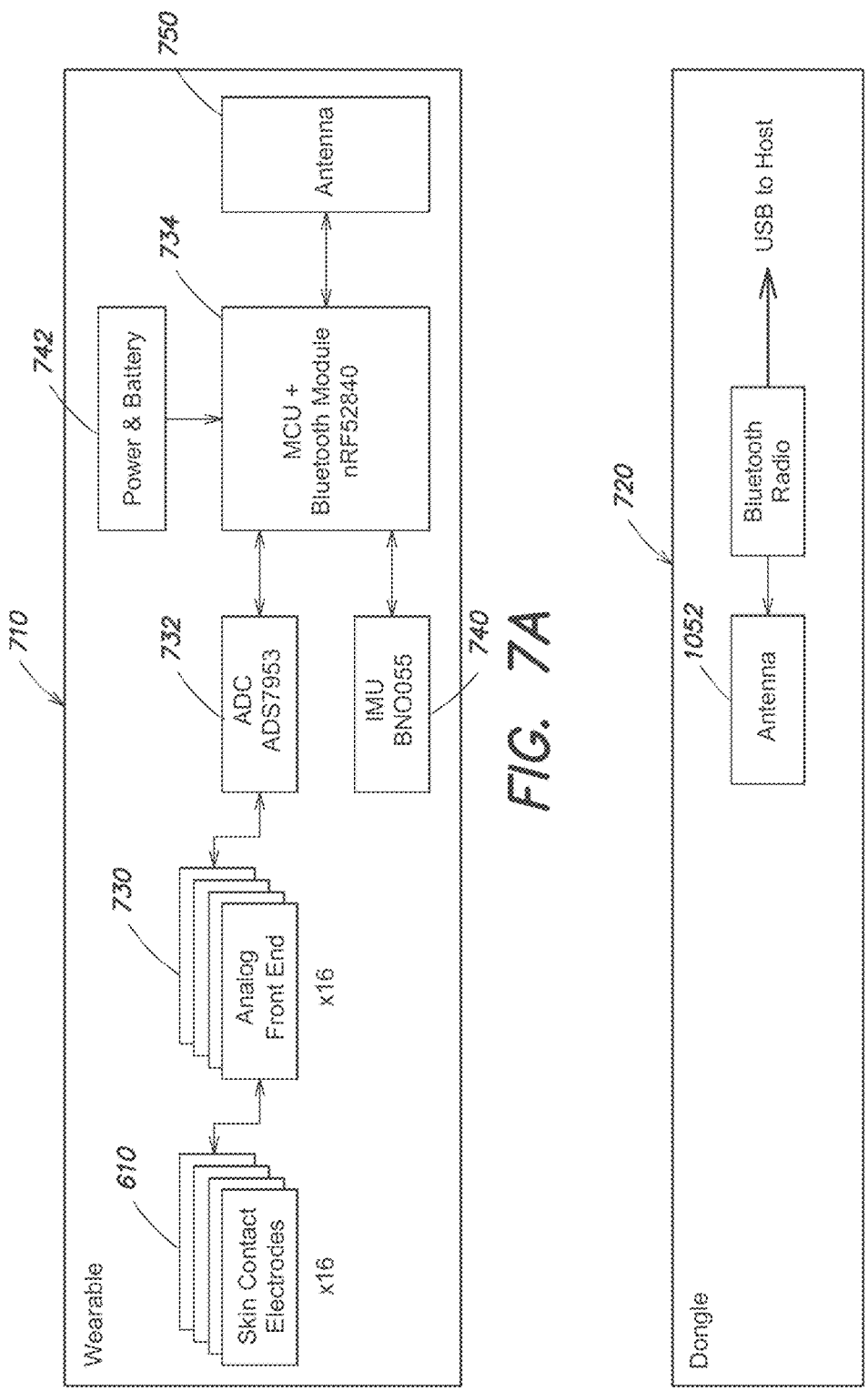
FIGS. 7A and 7B schematically illustrate components of a computer-based system on which some embodiments are implemented.

In some embodiments, the output of one or more of the sensing components can be optionally processed using hardware signal processing circuitry (e.g., to perform amplification, filtering, and/or rectification). In other embodiments, at least some signal processing of the output of the sensing components can be performed in software. Thus, signal processing of signals sampled by the sensors can be performed in hardware, software, or by any suitable combination of hardware and software, as aspects of the technology described herein are not limited in this respect. A non-limiting example of a signal processing chain used to process recorded data from sensors 610 is discussed in more detail below in connection with FIGS. 7A and 7B FIGS. 7A and 7B illustrate a schematic diagram with internal components of a wearable system with sixteen EMG sensors, in accordance with some embodiments of the technology described herein. As shown, the wearable system includes a wearable portion 710 (FIG. 7A) and a dongle portion 720 (FIG. 7B) in communication with the wearable portion 710 (e.g., via Bluetooth or another suitable short range wireless communication technology). As shown in FIG. 7A, the wearable portion 710 includes the sensors 610, examples of which are described in connection with FIGS. 6A and 6B. The output of the sensors 610 is provided to analog front end 730 configured to perform analog processing (e.g., noise reduction, filtering, etc.) on the recorded signals. The processed analog signals are then provided to analog-to-digital converter 732, which converts the analog signals to digital signals that can be processed by one or more computer processors. An example of a computer processor that may be used in accordance with some embodiments is microcontroller (MCU) 734 illustrated in FIG. 7A. As shown, MCU 734 may also include inputs from other sensors (e.g., IMU sensor 740), and power and battery module 742. The output of the processing performed by MCU may be provided to antenna 750 for transmission to dongle portion 720 shown in FIG. 7B.

Dongle portion 720 includes antenna 752 configured to communicate with antenna 750 included as part of wearable portion 710. Communication between antenna 750 and 752 may occur using any suitable wireless technology and protocol, non-limiting examples of which include radiofrequency signaling and Bluetooth. As shown, the signals received by antenna 752 of dongle portion 720 may be provided to a host computer for further processing, display, and/or for effecting control of a particular physical or virtual object or objects.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A computerized system configured to calibrate performance of one or more statistical models used to generate a musculoskeletal representation, the system comprising:
    a plurality of neuromuscular sensors configured to continuously record a plurality of neuromuscular signals, wherein the plurality of neuromuscular sensors are arranged on at least one wearable device; and
    at least one computer processor programmed to:
        process at least some of the plurality of neuromuscular signals using a statistical model to generate based, at least in part, on joint angle estimates and/or force estimates output from the statistical model, the musculoskeletal representation;
        determine based, at least in part, on at least one aspect of the musculoskeletal representation, that calibration of the statistical model used to generate the musculoskeletal representation is needed;
        initiate a calibration session in response to determining that calibration is needed;
        update a statistical model configuration based, at least in part, on a plurality of neuromuscular signals recorded by the plurality of neuromuscular sensors and ground-truth data representing position information and/or force information recorded during the calibration session to produce an updated statistical model;
        process at least some of the plurality of neuromuscular signals using the updated statistical model to generate an updated musculoskeletal representation;
        determine, based, at least in part, on the at least one aspect of the updated musculoskeletal representation whether further calibration of the statistical model is needed; and
        end the calibration session in response to determining that further calibration is not needed.

2. The computerized system of claim 1, wherein updating the statistical model configuration comprises selecting a different statistical model to generate the updated musculoskeletal representation than the statistical model used to generate to the musculoskeletal representation.

3. The computerized system of claim 1, further comprising:
    a user interface configured to instruct a user to perform at least one gesture during the configuration session,
    wherein the at least one computer processor is further programmed to control presentation of instructions via the user interface to instruct the user to perform the at least one gesture, and
    wherein updating the statistical model configuration is based, at least in part, on a plurality of neuromuscular signals recorded by the plurality of neuromuscular sensors during performance of the at least one gesture by the user.

4. The computerized system of claim 3, wherein the at least one computer processor is further programmed to update the statistical model configuration based, at least in part, on stored estimates of one or more of position information, force information, and neuromuscular information for the at least one gesture.

5. The computerized system of claim 3, wherein instructing the user to perform at least one gesture comprises instructing the user to perform a predetermined set of gestures.

6. The computerized system of claim 5 wherein controlling presentation of the instructions via the user interface comprises instructing the user to perform the gestures of the predetermined set in succession.

7. The computerized system of claim 1, wherein the at least one computer processor is further programmed to control at least one external device to capture the ground-truth data.

8. The computerized system of claim 7, wherein the at least one external device comprises an imaging device configured to capture at least one image, and wherein the ground-truth data is determined based, at least in part, on the at least one image.

9. The computerized system of claim 7, wherein the at least one external device comprises an inertial measurement unit.

10. The computerized system of claim 7, wherein the at least one external device comprises a plurality of external devices, each of which is configured to capture the position information or the force information of the ground-truth data.

11. The computerized system of claim 1, wherein updating the statistical model configuration comprises training the statistical model based, at least in part, on the plurality of neuromuscular signals recorded during the calibration session.

12. The computerized system of claim 1, wherein the statistical model is a trained statistical model, and wherein updating the statistical model configuration comprises adjusting one or more parameters provided as input to the trained statistical model without retraining the trained statistical model.

13. The computerized system of claim 1, wherein the at least one computer processor is further programmed to provide feedback to a user during the calibration session, wherein the feedback relates to the extent of a match between the updated musculoskeletal representation and the ground-truth data recorded during the calibration session.

14. The computerized system of claim 13, wherein providing feedback to the user comprises providing visual feedback.

15. The computerized system of claim 1, wherein determining that calibration is needed comprises identifying, based on the at least one aspect of the musculoskeletal representation, at least one gesture characteristic that the statistical model is poor at estimating.

16. The computerized system of claim 1, wherein the at least one computer processor is further programmed to render a visual representation associated with the hand based on the musculoskeletal representation and/or the updated musculoskeletal representation.

17. The computerized system of claim 16, wherein the visual representation is rendered during the calibration session.

18. The computerized system of claim 1, wherein the at least one computer processor is further programmed to:
  continuously track a calibration of a performance of the statistical model during usage of the statistical model following training; and
  initiate a calibration session when the calibration of the performance deviates from an acceptable calibration threshold by a particular amount.

19. The computerized system of claim 1, wherein updating the statistical model configuration comprises updating a plurality of model parameters, and wherein the at least one computer processor is further programmed to:
  store a user profile that includes user-specific calibration parameters, wherein the user-specific calibration parameters includes a subset of the plurality of model parameters.

20. The computerized system of claim 19, wherein the user-specific calibration parameters include at least one joint stiffness parameter.

21. A method of calibrating performance of one or more statistical models used to generate a musculoskeletal representation, the method comprising:
  recording a plurality of neuromuscular signals using a plurality of neuromuscular sensors arranged on at least one wearable device;
  processing at least some of the plurality of neuromuscular signals using a statistical model to generate based, at least in part, on joint angle estimates and/or force estimates output from the statistical model, the musculoskeletal representation;
  determining based, at least in part, on at least one aspect of the musculoskeletal representation, that calibration of the statistical model used to generate the musculoskeletal representation is needed;
  initiating a calibration session in response to determining that calibration is needed;
  updating a statistical model configuration based, at least in part on a plurality of neuromuscular signals recorded by the plurality of neuromuscular sensors and ground-truth data representing position information and/or force information recorded during the calibration session to produce an updated statistical model;
  processing at least some of the plurality of neuromuscular signals using the updated statistical model to generate an updated musculoskeletal representation;
  determining, based, at least in part, on the at least one aspect of the updated musculoskeletal representation whether further calibration of the statistical model is needed; and
  ending the calibration session in response to determining that further calibration is not needed.

22. A computerized system configured to calibrate performance of one or more statistical models used to generate a musculoskeletal representation, the system comprising:
  a user interface configured to instruct a user to perform at least one gesture while wearing a wearable device having a plurality of neuromuscular sensors arranged thereon; and
  at least one computer processor programmed to:
    control presentation of instructions via the user interface to instruct the user to perform the at least one gesture;
    update at least one parameter of the one or more statistical models based, at least in part, on a plurality of neuromuscular signals recorded by the plurality of neuromuscular sensors during performance of the at least one gesture by the user;
    identify, based on at least one aspect of the musculoskeletal representation generated based, at least in part, on joint angle estimates and/or force estimates output from the one or more statistical models, a plurality of gesture characteristics that the one or more statistical models is poor at estimating;
    select a new gesture for the user to perform that includes the identified plurality of gesture characteristics;
    control presentation of instructions via the user interface to instruct the user to perform the new gesture; and
    update at least one parameter of the one or more statistical models based, at least in part, on the plurality of neuromuscular signals recorded by the neuromuscular sensors during performance of the new gesture by the user.

23. The computerized system of claim 22, wherein the at least one computer processor is further programmed to update at least one parameter of the one or more statistical models based, at least in part, on stored estimates of one or more of position information, force information, and neuromuscular information for the at least one gesture.

24. The computerized system of claim 22, wherein the at least one computer processor is further programmed to:
  control at least one external device to capture at least one measurement of position and/or force information during performance of the at least one gesture; and update the at least one parameter of the one or more statistical models based, at least in part, on the at least one measurement of position and/or force information.

25. The computerized system of claim 22, wherein updating the at least one parameter of the one or more statistical models comprises training the one or more statistical models based, at least in part, on the plurality of neuromuscular signals recorded by the neuromuscular sensors during performance of the at least one gesture by the user.

26. The computerized system of claim 22, wherein the one or more statistical models includes a trained statistical model, and wherein updating the at least one parameter of the one or more statistical models comprises adjusting one or more parameters provided as input to the trained statistical model without retraining the trained statistical model.

27. The computerized system of claim 22, wherein the at least one computer processor is further programmed to provide feedback to the user, wherein the feedback indicates to the user whether the performance of the at least one gesture has been performed as instructed.

28. A method of calibrating performance of one or more statistical models used to generate a musculoskeletal representation, the method comprising:
instructing, via a user interface, a user to perform at least one gesture while wearing a wearable device having a plurality of neuromuscular sensors arranged thereon;
controlling presentation of instructions via the user interface to instruct the user to perform the at least one gesture;
updating at least one parameter of the one or more statistical models based, at least in part, on a plurality of neuromuscular signals recorded by the plurality of neuromuscular sensors during performance of the at least one gesture by the user;
identifying, based on at least one aspect of the musculoskeletal representation generated based, at least in part, on joint angle estimates and/or force estimates output from the one or more statistical models, a plurality of gesture characteristics that the one or more statistical models is poor at estimating;
selecting a new gesture for the user to perform that includes the identified plurality of gesture characteristics;
controlling presentation of instructions via the user interface to instruct the user to perform the new gesture; and
updating at least one parameter of the one or more statistical models based, at least in part, on the plurality of neuromuscular signals recorded by the neuromuscular sensors during performance of the new gesture by the user.

* * * * *